United States Patent
Manuel et al.

(10) Patent No.: US 11,344,421 B2
(45) Date of Patent: May 31, 2022

(54) METHODS AND INSTRUMENTATION FOR BALANCING OF LIGAMENTS IN FLEXION

(71) Applicants: Smith & Nephew, Inc., Memphis, TN (US); Smith & Nephew Orthopaedics AG, Zug (CH); Smith & Nephew Asia Pacific Pte. Limited, Singapore (SG)

(72) Inventors: Jacob B. Manuel, Austin, TX (US); Jennifer L. Johnson, Andover, MA (US)

(73) Assignees: Smith & Nephew, Inc., Memphis, TN (US); Smith & Nephew Orthopaedics AG, Zug (CH); Smith & Nephew Asia Pacific Pte. Limited, Singapore (SG)

(*) Notice: Subject to any disclaimer, the term of this patent is extended or adjusted under 35 U.S.C. 154(b) by 273 days.

(21) Appl. No.: 16/539,574

(22) Filed: Aug. 13, 2019

(65) Prior Publication Data
US 2020/0046509 A1     Feb. 13, 2020

Related U.S. Application Data

(60) Provisional application No. 62/718,151, filed on Aug. 13, 2018.

(51) Int. Cl.
*A61B 17/88*     (2006.01)
*A61B 17/56*     (2006.01)
(Continued)

(52) U.S. Cl.
CPC ........ *A61F 2/3886* (2013.01); *A61B 17/1764* (2013.01); *A61B 17/8866* (2013.01);
(Continued)

(58) Field of Classification Search
CPC ........ A61B 17/8866; A61B 2017/0268; A61B 2017/564; A61B 2017/565
See application file for complete search history.

(56) References Cited

U.S. PATENT DOCUMENTS 4,211,228 A * 7/1980 Cloutier .................. A61F 2/389
                                                         606/102
5,470,354 A * 11/1995 Hershberger .......... A61B 5/224
                                                         128/898

(Continued)

FOREIGN PATENT DOCUMENTS

WO     2012027511 A2     3/2012

OTHER PUBLICATIONS

Bellemans, J., et al., "Combined Technique for Journey II BCS and Journey II CR", Journey II TKA Total Knee System, p. 1-66, Retrieved from www.smith-nephew.com (2013).

*Primary Examiner* — Nicholas W Woodall
(74) *Attorney, Agent, or Firm* — KDB

(57) ABSTRACT

An exemplary method, and corresponding instrumentation, of balancing the ligaments of a knee during flexion is disclosed. In one embodiment, the method includes forming initial resection cuts in a patient' femur and tibia, and subsequently placing the knee in flexion to form a flexion space between the posterior femoral condyles and the resected tibial surface. The method may further include sequentially inserting one or more flexion spacers into the flexion space, and selecting the flexion spacer that provides the ligaments with equal tension. The flexion spacers may include a medial platform and a lateral platform wherein, for at least one of the flexion spacers, the lateral platform has a greater thickness than the medial platform. The method may further include engaging an alignment sizing tool with the selected flexion spacer, forming a pair of pin holes in the femur, and mounting a cutting block to the femur using the pin holes.

23 Claims, 17 Drawing Sheets

(51) Int. Cl.
  *A61B 17/02* (2006.01)
  *A61F 2/38* (2006.01)
  *A61B 17/17* (2006.01)
  *A61B 17/15* (2006.01)
  *A61F 2/46* (2006.01)

(52) U.S. Cl.
  CPC .......... *A61F 2/3859* (2013.01); *A61B 17/155* (2013.01); *A61B 17/157* (2013.01); *A61B 2017/0268* (2013.01); *A61B 2017/564* (2013.01); *A61B 2017/565* (2013.01); *A61F 2/4657* (2013.01); *A61F 2002/3863* (2013.01)

(56) References Cited

U.S. PATENT DOCUMENTS

| | | | |
|---|---|---|---|
| 6,758,850 B2 | 7/2004 | Smith et al. | |
| 8,167,888 B2* | 5/2012 | Steffensmeier | A61B 17/155 606/88 |
| 9,233,002 B2* | 1/2016 | Lenz | A61F 2/389 |
| 10,130,375 B2* | 11/2018 | Yager | A61B 17/1764 |
| 10,271,965 B2* | 4/2019 | Dungy | A61F 2/4657 |
| 2005/0143744 A1 | 6/2005 | Keeven et al. | |
| 2007/0173848 A1* | 7/2007 | Lennox | A61B 17/155 606/87 |
| 2007/0288032 A1* | 12/2007 | Metzger | A61F 2/4684 606/99 |
| 2010/0249790 A1 | 9/2010 | Roche | |
| 2010/0305711 A1* | 12/2010 | McKinnon | A61F 2/4684 623/20.32 |
| 2011/0087332 A1* | 4/2011 | Bojarski | A61B 17/1764 623/20.32 |
| 2013/0211411 A1* | 8/2013 | Tuke | A61B 17/1764 606/88 |
| 2013/0289570 A1* | 10/2013 | Chao | A61B 17/1764 606/88 |
| 2014/0243835 A1 | 8/2014 | Teeny et al. | |
| 2015/0088140 A1 | 3/2015 | Toler et al. | |
| 2019/0380721 A1* | 12/2019 | McMinn | A61B 17/155 |

\* cited by examiner

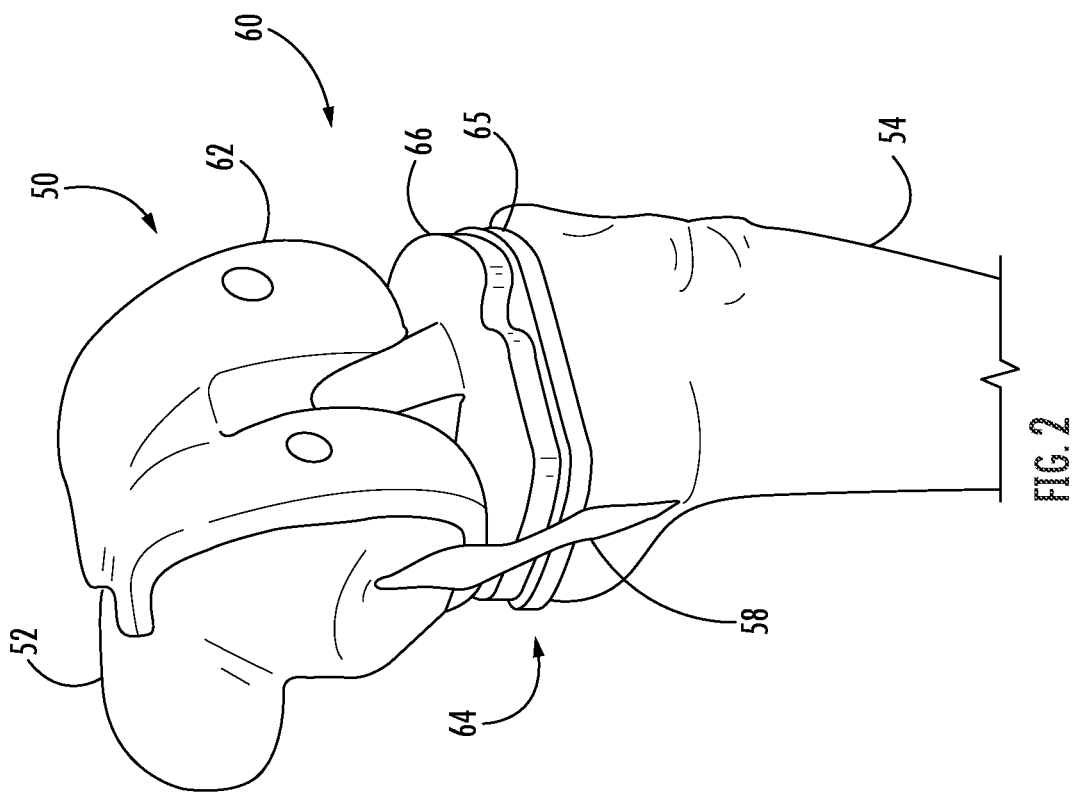
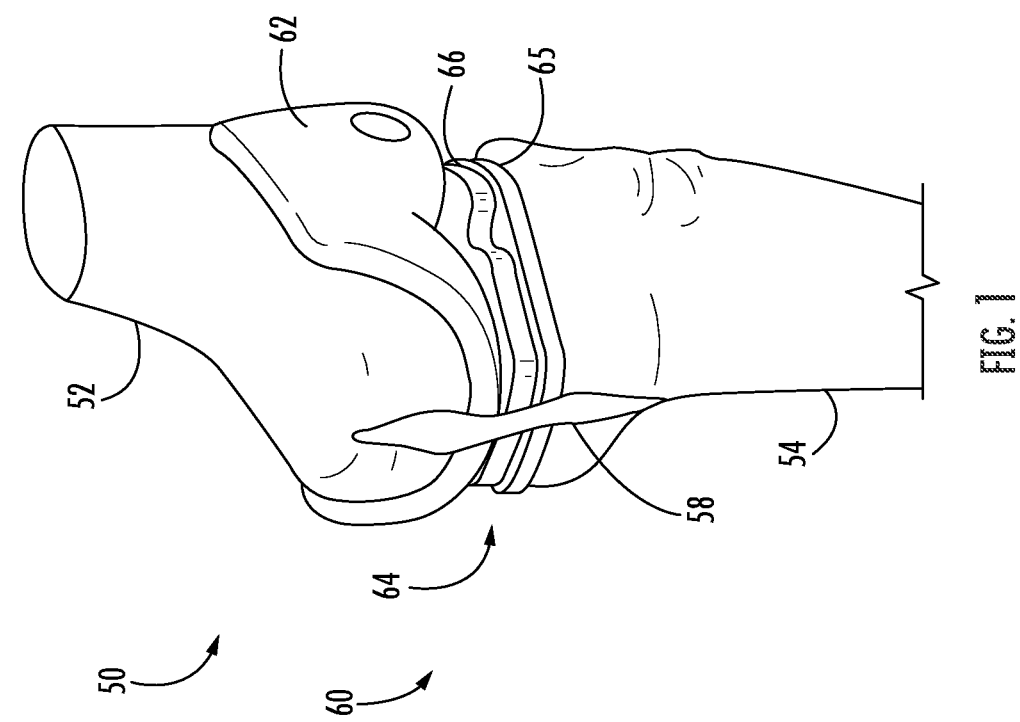

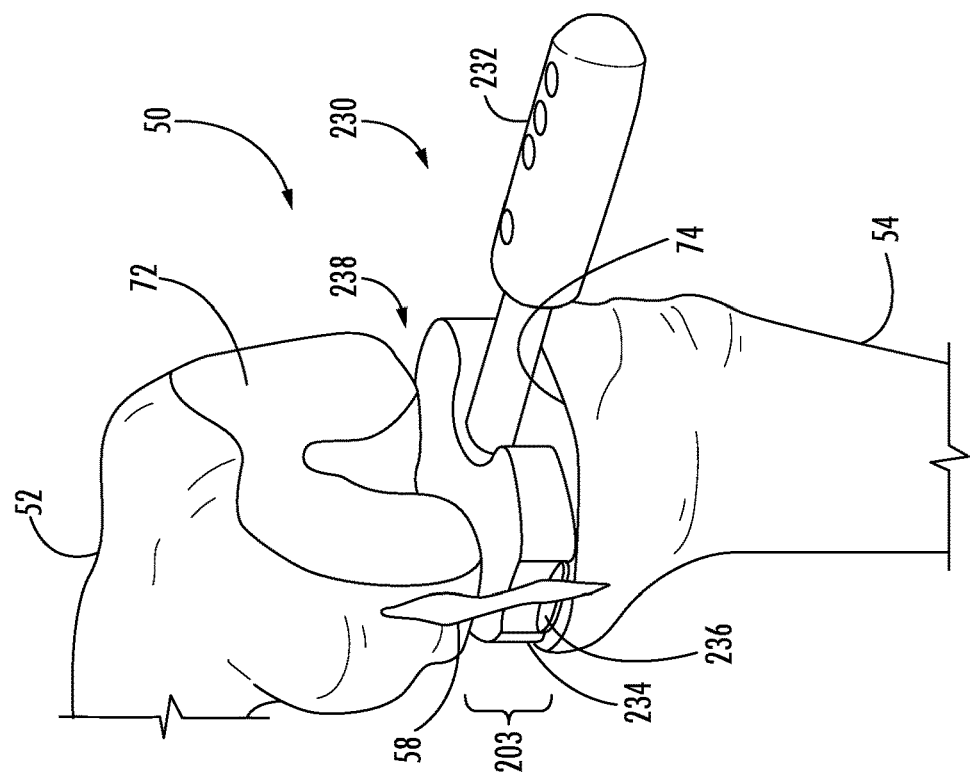
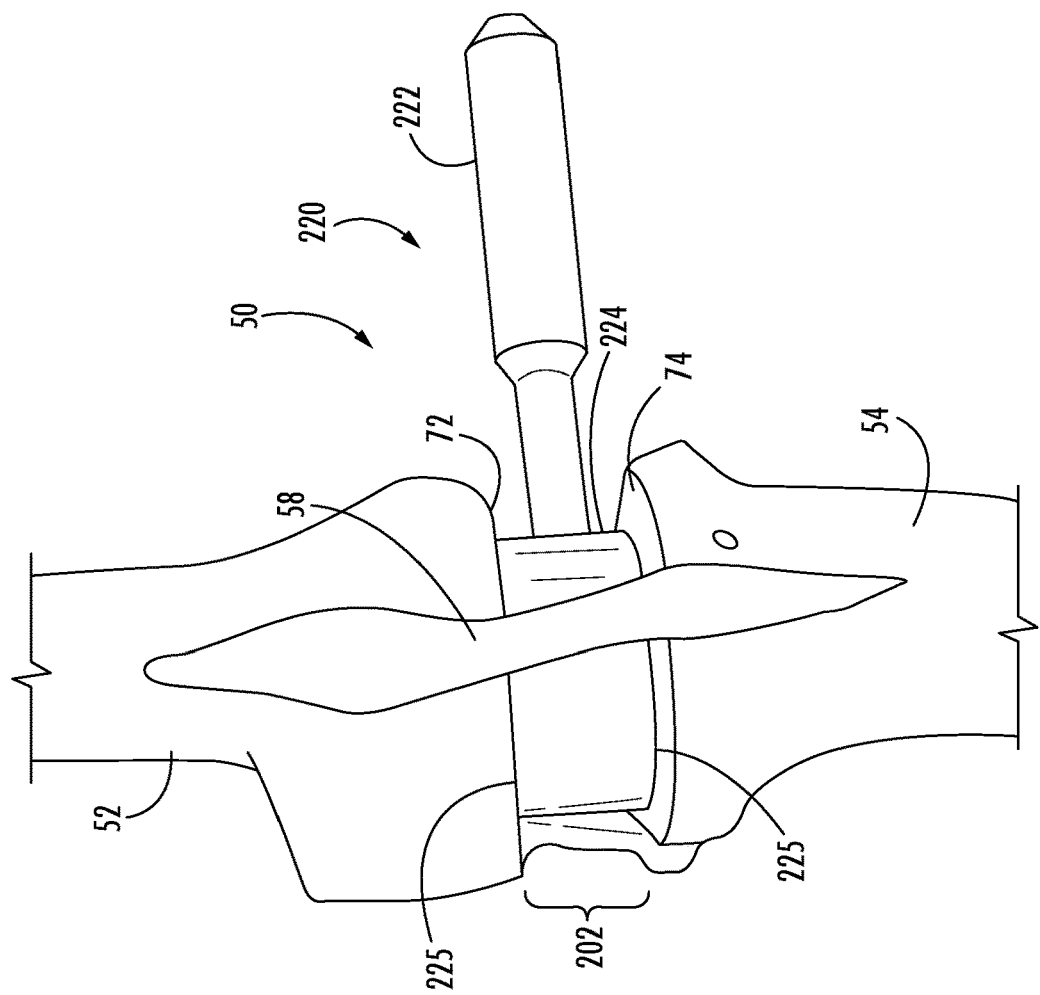

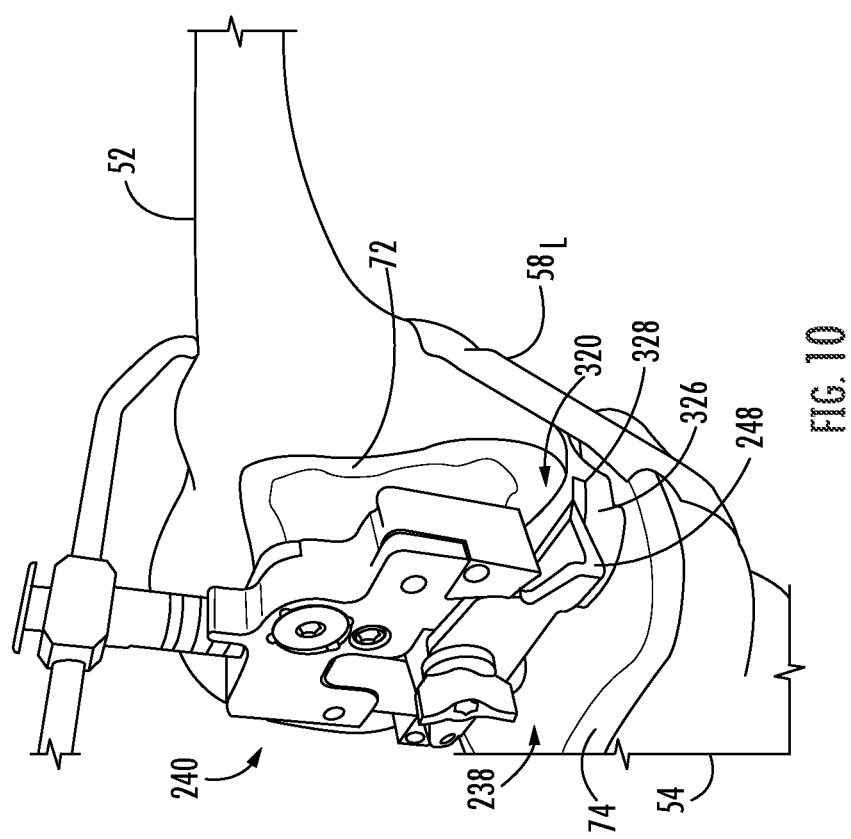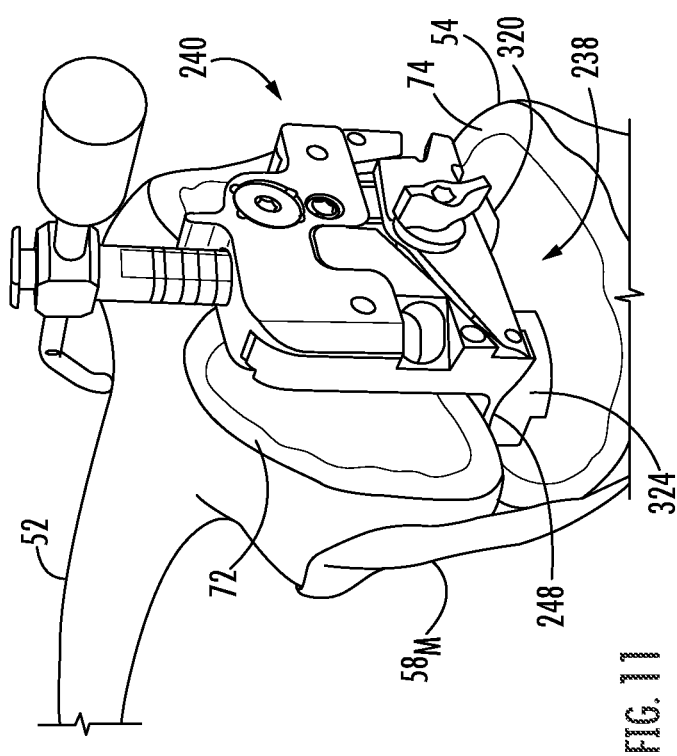

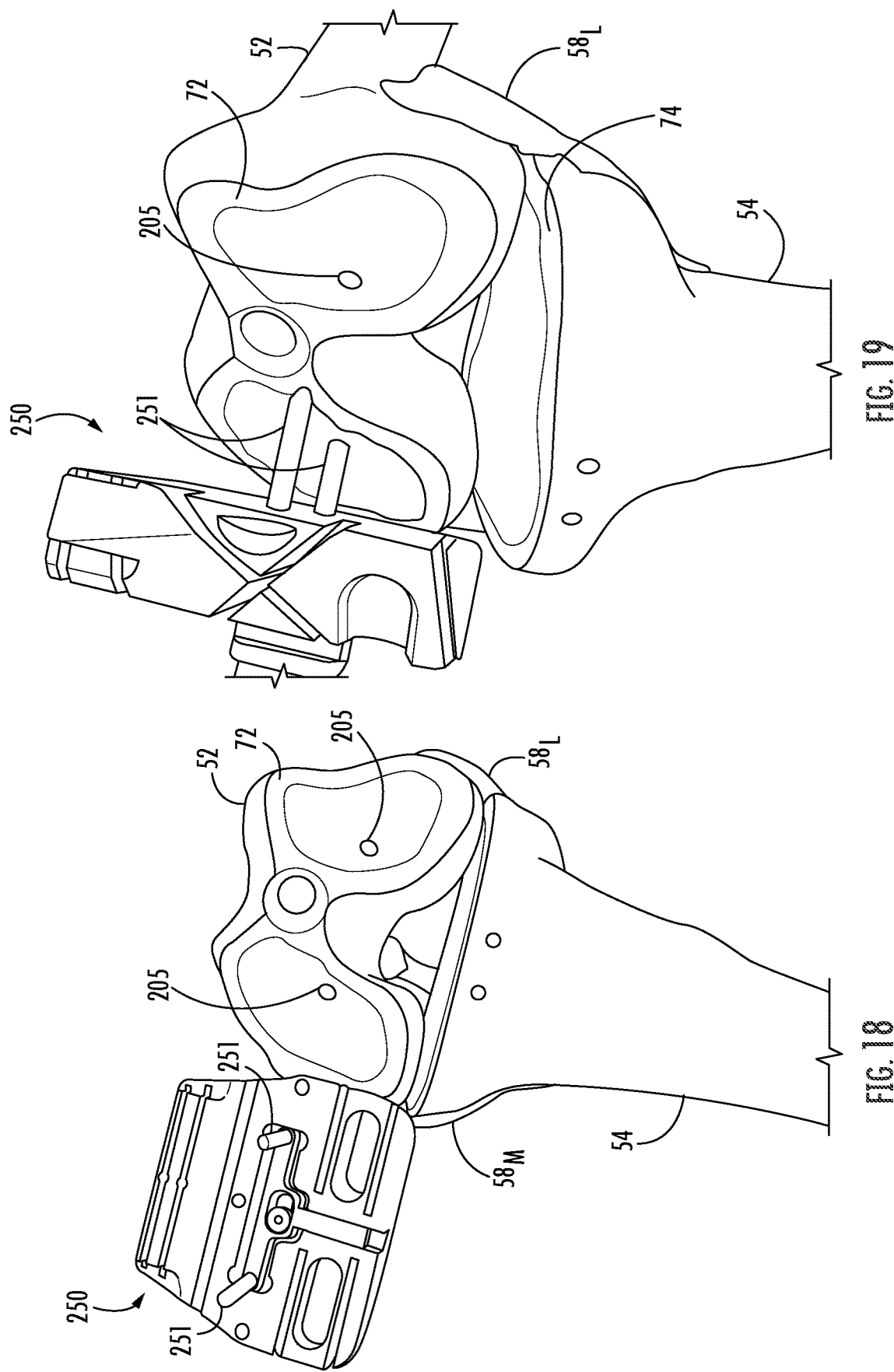

METHODS AND INSTRUMENTATION FOR BALANCING OF LIGAMENTS IN FLEXION

CROSS-REFERENCE TO RELATED APPLICATIONS

This application claims priority to, and the benefit of the filing date of, U.S. Provisional Patent Application Ser. No. 62/718,151, filed Aug. 13, 2018, entitled "Balancing of Ligaments in Flexion," the entire contents of which application is hereby incorporated in its entirety.

FIELD OF THE DISCLOSURE

The present disclosure relates generally to knee replacement systems and methods, and more particularly but not exclusively relates to systems and methods for balancing ligaments during total knee replacement procedures.

BACKGROUND OF THE DISCLOSURE

Generally speaking, in total knee replacement ("TKR") procedures, a surgeon typically uses rectangular spacer blocks to measure extension and flexion spaces after resecting portions of the patient's femur and tibia. This process often involves releasing one or more ligaments based on the spacing measurements in order to optimize balance. It has been found that this process can present difficulties, as releasing some soft tissue may affect extension only, releasing other soft tissue may affect flexion only, and releasing other soft tissue may affect both flexion and extension. Additionally, it is often difficult to achieve or even determine the proper ligament tension, particularly when attempting to do so with the requirement that the flexion space remain substantially rectangular.

Additional difficulties can arise in connection with the fact that the medial condyle in a patient's knee is typically subject to a greater degree of wear than the lateral condyle. Many knee implant systems are designed such that the medial condyle has a predetermined and constant depth of cut for the resection. Due to the fact that the amount of wear is variable, however, this can lead to varying depths of resection cuts on the lateral condyle. This hinders the balancing of the flexion gap, and often prevents such balance from being achieved.

For these reasons among others, there remains a need for further improvements in this technological field.

SUMMARY OF THE DISCLOSURE

This Summary is provided to introduce a selection of concepts in a simplified form that are further described below in the Detailed Description. This Summary is not intended to identify key features or essential features of the claimed subject matter, nor is it intended as an aid in determining the scope of the claimed subject matter.

The present disclosure provides an exemplary method involves balancing the ligaments of a knee during flexion. The method involves forming initial resection cuts in the femur and the tibia, and subsequently placing the knee in flexion to form a flexion space between the posterior femoral condyles and the resected tibial surface. The method further includes sequentially inserting one or more flexion spacers into the flexion space, and selecting the flexion spacer that provides the ligaments of the knee with equal tension. Each of the flexion spacers includes a medial platform and a lateral platform. For at least one of the flexion spacers, the lateral platform has a greater thickness than the medial platform. The method further includes engaging an alignment sizing instrument with the selected flexion spacer, forming a pair of pin holes in the femur using the alignment sizing instrument, and mounting a cutting block to the femur using the pin holes.

Provided herein is a method of balancing ligaments in a knee joint including a femur and a tibia, the method comprising: forming a distal cut in the femur, thereby defining a femoral resection surface; forming a proximal cut in the tibia, thereby defining a tibial resection surface; placing the knee joint in flexion and, with the knee joint in flexion, assessing a flexion space formed between posterior condyles of the femur and the tibial resection surface, wherein assessing the flexion space comprises: sequentially inserting one or more flexion spacers into the flexion space until the ligaments have equal tension; and selecting the flexion spacer that provides the ligaments with equal tension; wherein each of the flexion spacers comprises a medial platform and a lateral platform; wherein for one of the flexion spacers, the medial platform has a medial platform thickness and the lateral platform has a first lateral platform thickness greater than the medial platform thickness; with the selected tension spacer inserted into the flexion space, engaging an alignment sizing instrument with the selected tension spacer and bringing the alignment sizing instrument into contact with the femoral resection surface, wherein the alignment sizing instrument includes a pair of guide holes; forming a pair of pin holes in the femur utilizing the pair of guide holes; mounting a cutting block to the femur, wherein mounting the cutting block to the femur comprises placing a pair of pins in the pair of pin holes, and wherein the cutting block includes at least one guide slot; forming at least one additional resection cut in the femur, wherein forming the at least one additional resection cut comprises guiding a cutting instrument with the at least one guide slot; after forming the at least one additional resection cut, implanting a femoral component to the resected femur; and implanting a tibial component to the resected tibia.

In certain embodiments, the tibial component comprises a tibial tray component and an insert mounted to the tibial tray component, and wherein the method further comprises selecting the insert from an insert family based at least in part upon the selected flexion spacer, wherein the insert family comprises a plurality of insert species, and wherein each insert species has a different thickness.

In certain embodiments, the method further comprises placing the knee joint in extension and, with the knee joint in extension, assessing an extension space formed between the femoral resection surface and the tibial resection surface, wherein assessing the extension space involves inserting extension spacers of different sizes into the extension space until the ligaments have equal tension.

In certain embodiments, each extension spacer comprises a pair of parallel bone-facing surfaces, wherein assessing the extension space involves placing the bone-facing surfaces of one or more of the extension spacers in contact with the femoral resection surface and the tibial resection surface.

In certain embodiments, each of the extension spacers comprises an extension spacer block, wherein each of the extension spacers further comprises a corresponding shim, and wherein the method further comprises forming one or more of the extension spacers by combining the extension spacer block with the shim corresponding to the extension spacer.

In certain embodiments, the method further comprises selecting the extension spacer that provides the ligaments with equal tension, wherein selecting the insert is based in part upon the selected extension spacer.

In certain embodiments, selecting the insert comprises: selecting a first insert species of the plurality of insert species based upon the selected flexion spacer; selecting a second insert species of the plurality of insert species based upon the selected extension spacer; if the first insert species and the second insert species are one species, selecting the one species for the insert; if the first insert species is of a greater thickness than the second insert species, selecting the first insert species for the insert; and if the first insert species is of a lesser thickness than the second insert species, selecting the second insert species for the insert.

In certain embodiments, the first insert species is of a greater thickness than the second insert species, and the method further comprises removing additional bone from the femur until the extension space is of a size corresponding to the first insert species.

In certain embodiments, the second insert species is of a greater thickness than the first insert species, and the method further comprises shifting the guide holes anteriorly prior to forming the pair of pin holes.

In certain embodiments, the method further comprises forming the two or more flexion spacers, wherein forming each flexion spacer comprises: selecting a flexion spacer block from a plurality of flexion spacer blocks; selecting a shim from a plurality of shims; and coupling the selected flexion spacer block with the selected shim.

In certain embodiments, the first medial platform thickness is equal to the first lateral platform thickness.

In certain embodiments, the first lateral platform thickness is greater than the first medial platform thickness.

In certain embodiments, for another of the flexion spacers, the medial platform has the medial platform thickness and the lateral platform has a second lateral platform thickness less than the first lateral platform thickness.

In certain embodiments, for the one of the flexion spacers: the lateral platform includes a slot having a first engagement surface; the medial platform defines a second engagement surface; and the first engagement surface and the second engagement surface are coplanar.

In certain embodiments, the selected flexion spacer is the one of the flexion spacers, and wherein engaging the alignment sizing instrument with the selected flexion spacer comprises engaging a first leg of the alignment sizing instrument with the first engagement surface and engaging a second leg of the alignment sizing instrument with the second engagement surface.

In certain embodiments, the first engagement surface is an upper surface of the medial platform and wherein the second engagement surface is a lower surface of the slot.

In certain embodiments, the ligaments comprise a medial cruciate ligament and a lateral cruciate ligament, wherein sequentially inserting the two or more flexion spacers into the flexion space comprises inserting the other of the flexion spacers first, and in response to the lateral cruciate ligament having less tension the medial cruciate ligament, removing the other of the flexion spacers and inserting the one of the flexion spacers, thereby increasing tension in the lateral cruciate ligament.

In certain embodiments, inserting each flexion spacer into the flexion space comprises: engaging a lower surface of the flexion spacer with the tibial resection surface; engaging an upper surface of the medial platform with a posterior medial condyle of the femur; and engaging an upper surface of the lateral platform with a posterior lateral condyle of the femur.

In certain embodiments, with the one of the flexion spacers inserted into the flexion space, the femur has a first position relative to the tibia; wherein with the other of the flexion spacers inserted into the flexion space, the femur has a second position relative to the tibia; and wherein the second position is rotationally offset from the first position.

In certain embodiments, the at least one guide slot includes an anterior guide slot, a posterior guide slot, an anterior chamfer guide slot, and a posterior chamfer guide slot; and wherein forming the at least one additional resection cut comprises forming an anterior cut using the anterior guide slot, forming a posterior cut using the posterior guide slot, forming an anterior chamfer cut using the anterior chamfer guide slot, and forming a posterior chamfer cut using the posterior chamfer guide slot.

Provided herein is a kit of spacer blocks for implantation into a patient's knee during a total knee replacement procedure, the kit comprising: a plurality of spacer blocks including at least a first spacer block and a second spacer block, wherein: the first spacer block includes a body portion, a medial platform positioned on a medial side of the body portion, and a lateral platform positioned on an opposite lateral side of the body portion, the medial platform including a first medial platform thickness, the lateral platform including a first lateral platform thickness; the second spacer block includes a body portion, a medial platform positioned on a medial side of the body portion, and a lateral platform positioned on an opposite lateral side of the body portion, the medial platform including a second medial platform thickness, the lateral platform including a second lateral platform thickness; the second medial platform thickness is equal to the first medial platform thickness, the second lateral platform thickness is greater than the first lateral platform thickness so that the second spacer block is arranged and configured to rotate a patient's femur during use.

In certain embodiments, the first lateral platform thickness is greater than the first medial platform thickness.

In certain embodiments, the thicknesses of the first lateral platform and the first medial platform are arranged and configured to provide one degree of rotation during use.

In certain embodiments, the thicknesses of the second lateral platform and the second medial platform are arranged and configured to provide three degrees of rotation during use.

In certain embodiments, a third spacer block is provided, the third spacer block including a body portion, a medial platform positioned on a medial side of the body portion, and a lateral platform positioned on an opposite lateral side of the body portion, the medial platform including a third medial platform thickness, the lateral platform including a third lateral platform thickness; wherein the third medial platform thickness is equal to the first and second medial platform thicknesses, the third lateral platform thickness is greater than the first and second lateral platform thicknesses so that the third spacer block is arranged and configured to provide increased rotation of the patient's femur relative to the first and second spacer blocks during use.

In certain embodiments, the lateral platform of the second spacer block includes a receiving slot having a top and bottom surface, the bottom surface of the receiving slot being arranged and configured to be coplanar with an upper surface of the medial platform of the second spacer block.

In certain embodiments, the first and second spacer blocks further comprise a cavity configured to couple to a handle of a flexion gap assessment instrument.

In certain embodiments, the first medial platform thickness is arranged and configured to correspond to a combined thickness of a baseplate of a tibial tray component and a first insert.

In certain embodiments, a plurality of shims is provided, the plurality of shims including at least a first shim and a second shim, the first shim including a first shim thickness, the second shim including a second shim thickness, the second shim thickness being greater than the first shim thickness, wherein each of the first and second spacer blocks are arranged and configured to receive each of the first and second shims.

The embodiments disclosed herein may provide for certain advantages over conventional approaches. Currently, surgeons use a rectangular spacer block to measure both the extension space and the flexion space, or may use a mechanical tensioner. These spacer blocks and tensioners may be used after all the resection cuts have been made. Surgeons size the femur and set the rotation of the femoral implant off a femoral alignment sizing instrument. Mechanical tensioners may then be used. However, one problem with using conventional tensioners is that they pivot about the center point as opposed to maintaining a constant height of the medial portion. In such approaches, should the extension and flexion spaces be non-rectangular, the surgeon typically must perform to do soft tissue releases to balance the knee. In the embodiments disclosed herein, however, the surgeon is able to balance the flexion space and set rotation and placement of the AP cutting block prior to making any rotational femoral cuts. This may reduce or eliminate the need to perform soft tissue adjustments for balancing.

Further features and advantages of at least some of the embodiments of the present invention, as well as the structure and operation of various embodiments of the present invention, are described in detail below with reference to the accompanying drawings.

BRIEF DESCRIPTION OF THE DRAWINGS

By way of example, a specific embodiment of the disclosed device will now be described, with reference to the accompanying drawings, in which:

FIG. 1 illustrates a perspective view of a patient's knee including an example of an embodiment of a knee trial assembly coupled to the knee, the knee shown in extension;

FIG. 5 illustrates a side view of a partially-resected knee with an example of an embodiment of an extension space measurement tool positioned between the patient's femur and tibial in accordance with certain principles of the present disclosure, the knee shown in extension;

FIG. 6 illustrates a side perspective view of the partially-resected knee shown in FIG. 5 with a flexion space measurement instrument positioned between the patient's femur and tibial in accordance with certain principles of the present disclosure, the knee shown in flexion;

FIGS. 10 and 11 illustrate various perspective views of the partially-resected knee shown in FIG. 5 with the alignment sizing instrument and the flexion spacer shown in FIG. 7, the knee shown in flexion;

FIG. 12 illustrate various perspective views of examples of an embodiment of a flexion spacer block family in accordance with certain principles of the present disclosure;

FIGS. 18 and 19 illustrate various perspective views of the partially-resected knee along with an example of an embodiment of a cutting block in accordance with certain principles of the present disclosure.

Figure 4:
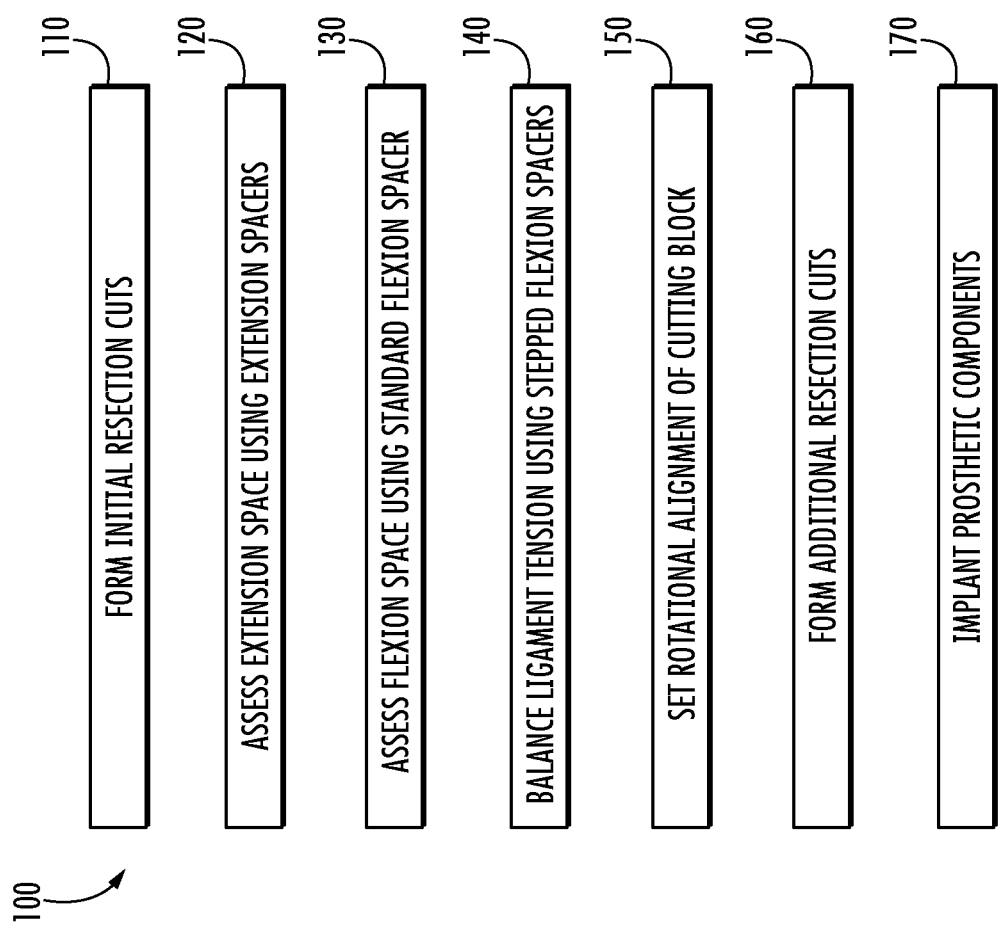
FIG. 4 is a schematic flow diagram of an example of an embodiment of a method in accordance with the principles of the present disclosure.

The drawings are not necessarily to scale. The drawings are merely representations, not intended to portray specific parameters of the disclosure. The drawings are intended to depict various embodiments of the disclosure, and therefore are not to be considered as limiting in scope. In the drawings, like numbering represents like elements.

DETAILED DESCRIPTION

Embodiments of an improved method for balancing a patient's ligaments in a total knee replacement procedure including corresponding instrumentation will now be described more fully hereinafter with reference to the accompanying drawings, in which preferred embodiments of the present disclosure are presented. As will be described and illustrated, in some embodiments, the method involves balancing the ligaments of a knee during flexion, extension, and/or both. In some embodiments, the method involves forming initial resection cuts in the femur and the tibia, and subsequently placing the knee in flexion and sequentially inserting one or more flexion spacers into the flexion space, and selecting the flexion spacer that provides the ligaments of the knee with equal tension. The example method and corresponding instrumentation of the present disclosure may, however, be embodied in many different forms and should not be construed as being limited to the embodiments set forth herein. Rather, these embodiments are provided so that this disclosure will convey certain example embodiments of the method and devices to those skilled in the art. In the drawings, like numbers refer to like elements throughout unless otherwise noted.

Figure 2:
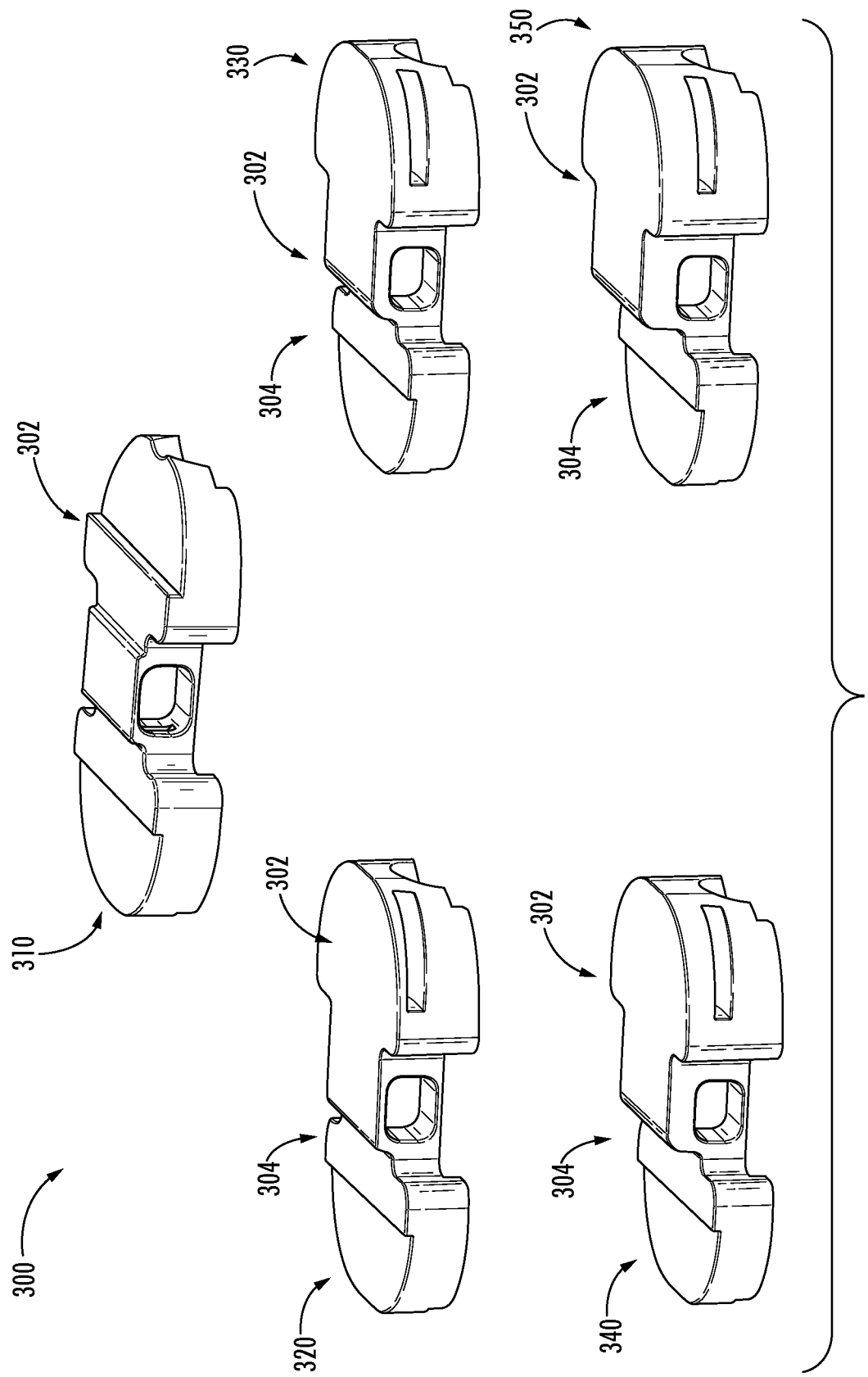
FIG. 2 illustrates an alternate perspective view of the knee and trial assembly shown in FIG. 1, the knee shown in flexion.

With reference to FIGS. 1 and 2, illustrated therein is an example of an embodiment of a knee joint 50, the knee joint 50 undergoing a total knee replacement (TKR) procedure. FIGS. 1 and 2 illustrate a trial implant assembly 60 implanted to the knee joint 50. More particularly, FIG. 1 illustrates the knee joint 50 in extension, and FIG. 2 illustrates the knee joint 50 in flexion. As will be readily understood by one of ordinary skill in the art, the knee joint 50 includes a femur 52, a tibia 54, and ligaments 58.

As illustrated, generally speaking, the trial implant assembly 60 includes a femoral component 62 and a tibial component 64. During the TKR procedure, the distal end of the femur 52 is resected and the femoral component 62 is implanted thereto, and the proximal end of the tibia 54 is resected and the tibial component 64 is implanted thereto. As illustrated, the tibial component 64 may include a tibial tray component 65 implanted to the proximal end of the tibia 54 and an insert 66 mounted to the tibial tray component 65. The insert 66 interfaces with the femoral component 62 to define an articular interface that facilitates pivoting of the knee joint between flexion and extension. As will be described in greater detail herein, the insert 66 may be selected from a family of inserts, each of which has a different thickness.

In a healthy knee joint, the femur and the tibia cooperate with the cruciate ligaments and other soft tissue to facilitate extension and flexion of the knee joint in a manner that feels natural to a person. As will be appreciated, the efficacy of a TKR procedure in achieving results that feel natural to the patient depends upon several factors, including the tension experienced by the ligaments during flexion and extension. Improper balancing of the tension in the ligaments can lead not only to reduced patient satisfaction with the movement of the knee, but also to increased wear and poorer long-term results. Thus, it would be desirable to ensure that the tension in the ligaments is balanced in both tension and flexion.

Figure 3:
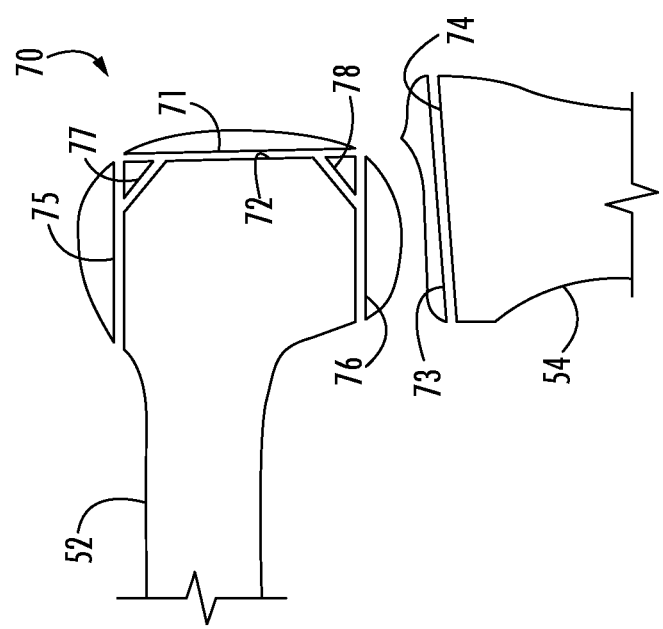
FIG. 3 illustrates a schematic representation of an example of an embodiment of a plurality of cuts formed in a patient's femur and tibial during a total knee replacement procedure in accordance with the principles of the present disclosure.

With additional reference to FIG. 3, illustrated therein is an example of an embodiment of a plurality of resection cuts 70 formed during a typical TKR procedure. The resection cuts 70 generally include a distal femur cut 71 that defines a distal femoral resection surface 72 for the femur 52, and a proximal tibia cut 73 that defines a proximal tibial resection surface 74 for the tibia 54. These initial resection cuts 71, 73 (e.g., distal femur cut 71 and proximal tibia cut 73) may be formed first. Thereafter, a four-in-one anterior-posterior cutting block may be secured to the femur 52 to form the remaining cuts, including the anterior femur cut 75, the posterior femur cut 76, and anterior and posterior chamfer cuts 77, 78. Alternatively, the proximal tibia cut 73 may be formed after all of the distal cuts 71, 75, 76, 77, 78 are formed.

With reference to FIG. 4, illustrated herein is an example of an embodiment of a method or process 100 (used interchangeably herein without the intent to limit) in accordance with certain principles of the present disclosure. Operations illustrated for the method/process in the present application are understood to be examples only, and operations may be combined or divided, and added or removed, as well as re-ordered in whole or in part, unless explicitly stated to the contrary.

The illustrated process 100 may include operation 110, which generally involves forming the initial resection cuts in the femur 52 and tibia 54. More particularly, the operation 110 involves forming the distal femur cut 71 in the femur 52 and the proximal tibia cut 73 in the tibia 54, thereby defining the distal femoral resection surface 72 and the proximal tibial resection surface 74. The manner in which these cuts are formed is known in the art, and need not be described in detail herein. With the initial resection cuts 71, 73 formed, the process 100 continues to operation 120.

Figure 5A:
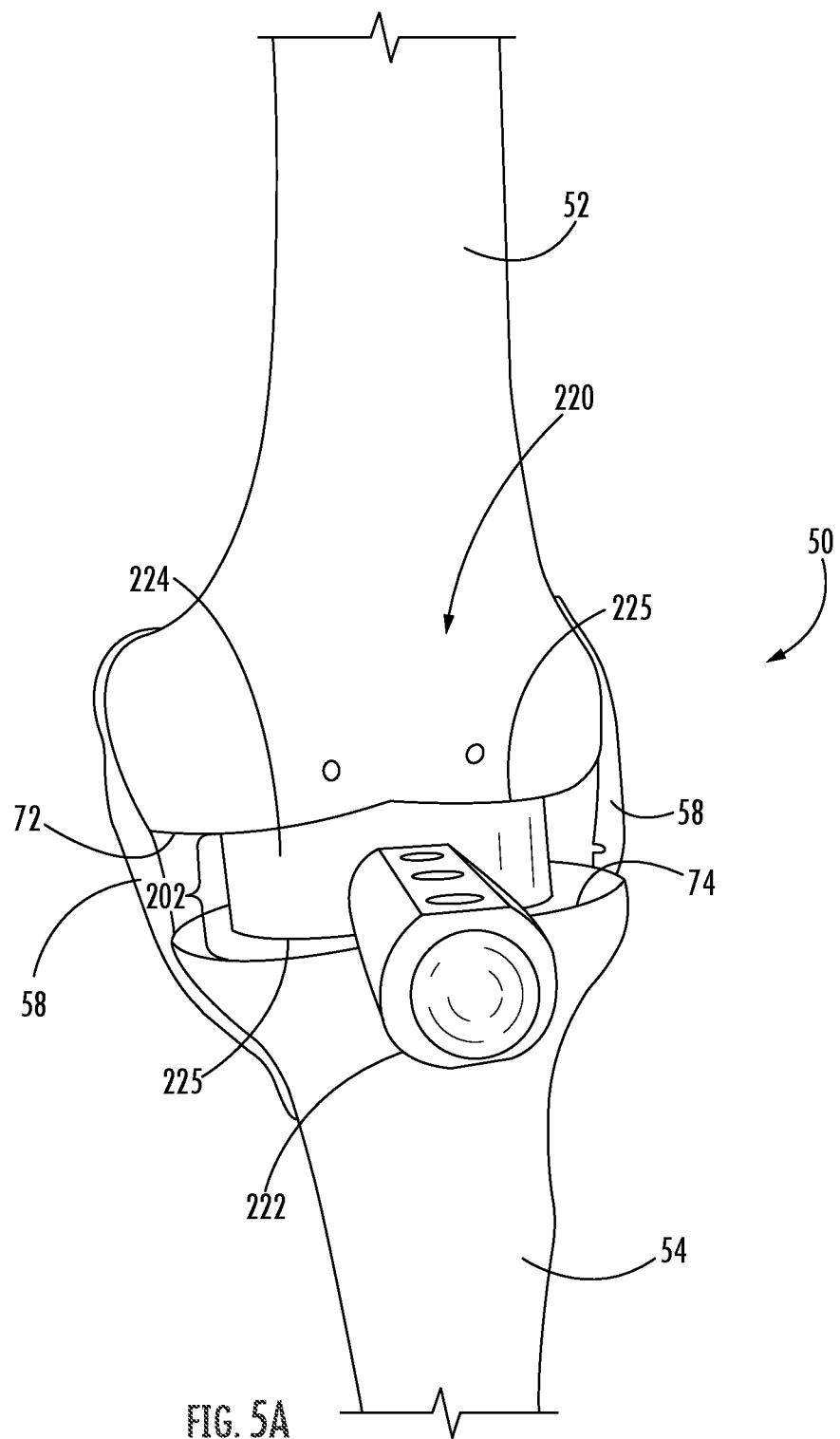
FIG. 5A illustrates a front view of the partially-resected knee shown in FIG. 5 with the extension space measurement instrument positioned between the patient's femur and tibial in accordance with certain principles of the present disclosure, the knee shown in extension.

With additional reference to FIGS. 5 and 5A, operation 120 (FIG. 4) generally involves assessing the extension space 202 for the TKR procedure. The operation 120 involves placing the knee joint 50 in extension such that the femur 52 is generally aligned with the tibia 54, and separating the femur 52 from the tibia 54 such that the extension space 202 is formed between the femoral resection surface 72 and the tibial resection surface 74. An extension space measurement instrument 220 may be used to determine the height of the space 202 (e.g., the distance between the femoral resection surface 72 and the tibial resection surface 74—the height is equal to the distal femur implant thickness and the tibial implant thickness (i.e., tray and insert)). As illustrated, the extension space measurement instrument 220 may include a handle 222 and an extension gap measurement block 224 releasably coupled to the handle 222.

The extension gap measurement block 224 may include a pair of parallel bone-facing surfaces 225 that are offset by a known distance. As such, each extension gap measurement block 224 generally includes a known height. More particularly, in use, the known distance corresponds to the combined thickness of the distal portion of the femoral component 62, the baseplate of the tibial tray component 65, and the thinnest species of the insert 66. Thus, when the extension gap measurement block 224 is inserted into the space 202, it is known that there is sufficient space for the trial implant assembly 60, and subsequently the knee implant assembly, to be implanted into the knee joint 50. If the extension space 202 is not balanced and/or the ligaments 58 are under too much tension, the surgeon may increase the dimension of the extension space 202 by removing additional bone and/or releasing one or more of the ligaments 58.

If the extension gap measurement block 224 does not fit snugly within the extension space 202 (e.g., the extension gap measurement block 224 is too small), the surgeon may reiterate operation 120 with extension gap measurement blocks 224 of increasing size until appropriate tension and balance is achieved. Each extension gap measurement block 224 may have an increasing size (e.g., height) corresponding to a respective species of an insert 66. Alternatively, a single extension gap measurement block 224 may be utilized in combination with one or more shims such as, for example, shims 402 (FIG. 12) having varying thicknesses or the like, where each thickness corresponds to a respective species of the insert 66. Once appropriate tension in the ligaments has been achieved, the height of the corresponding extension gap measurement block 224 is noted as the appropriate dimension for the extension space 202, and the corresponding species of insert 66 is noted, selected, or the like.

Figure 16:
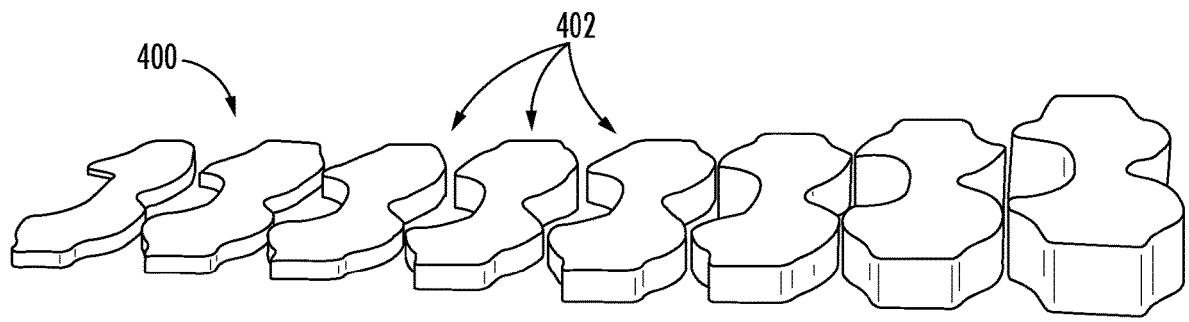
FIG. 16 illustrate a perspective view of an example of an embodiment of a shim family in accordance with certain principles of the present disclosure.

With additional reference to FIG. 6, the process 100 may further include operation 130 (FIG. 4), which involves assessing a flexion space 203 with the native posterior femoral condyles intact. Operation 130 is performed using a flexion gap assessment instrument 230 including a handle 232 and a flexion gap spacer 238 releasably coupled to the handle 232. The flexion gap spacer 238 may include a flexion spacer block 234 releasably coupled to the handle 232, and may further include a shim 236 releasably coupled to the flexion spacer block 234. As will be described in greater detail herein, the flexion spacer block 234 may be selected from a spacer block family 300 including spacer blocks 302 having varying dimensional characteristics (FIG. 12), and the shim 236 may be selected from a shim family 400 including shims 402 having varying dimensional characteristics (FIG. 16). Operation 130 may involve selecting a flexion spacer block 234 and a shim 236 such that when the flexion gap spacer 238 is placed between the posterior femoral condyles and the resected proximal tibial surface 74, the ligaments 58 are provided with balanced tension.

Figure 7:
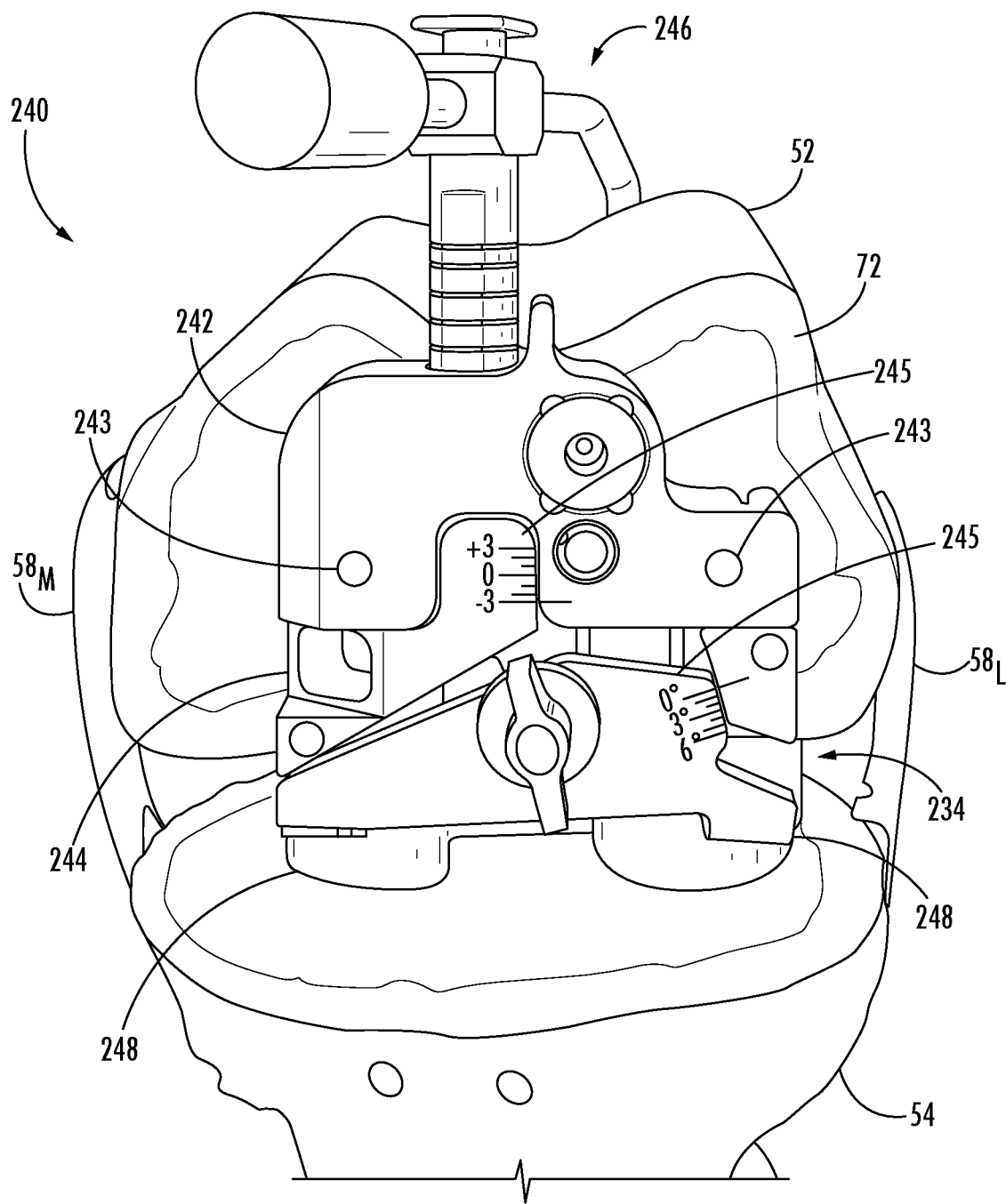
FIG. 7 illustrates the partially-resected knee shown in FIG. 5 with an example of an embodiment of an alignment sizing instrument and the flexion spacer positioned between the patient's femur and tibial in accordance with certain principles of the present disclosure, the knee shown in flexion.

With additional reference to FIG. 7, the process 100 may further involve using a femoral sizing instrument 240. Alternatively, the process 100 may use any other now known or hereafter developed method or mechanism for developing the pin holes 205, which place the pin holes in the same orientations as the femoral sizing instrument 240. For example, a drill guide could be used. In use, the drill guide could be attached to the handle 222, 232 since the handle is a known dimension from the medial surface. Alternatively, we could utilize a drill guide that could be coupled to the flexion spacer block. In one example of an embodiment, as illustrated, a femoral sizing instrument 240 can be used. The femoral sizing instrument 240 may include a first body portion 242, a second body portion 244 movably coupled with the first body portion 242, a stylus 246 movably mounted to the first body portion 242, and a pair of paddles 248 extending from the second body portion 244. The first body portion 242 may include a pair of guide holes 243 that can be used to form pin holes 205 in the femur 52 (FIG. 18). As will be described in greater detail herein, the pin holes 205 may be used to align the anterior-posterior (AP) cutting block 250 used to create the additional resection cuts 75, 76, 77, 78, and may further receive pegs of the femoral component 62 to align and partially secure the femoral component 62 to the femur 52. The first body portion 242 may also include an indicator, and the second body portion 244 may include a scale 245 that cooperates with the indicator to indicate a relative position of the first and second body portions 242, 244. Once an appropriate relative position has been achieved, the relative position may be locked in place by tightening a set screw 241.

Figure 8:
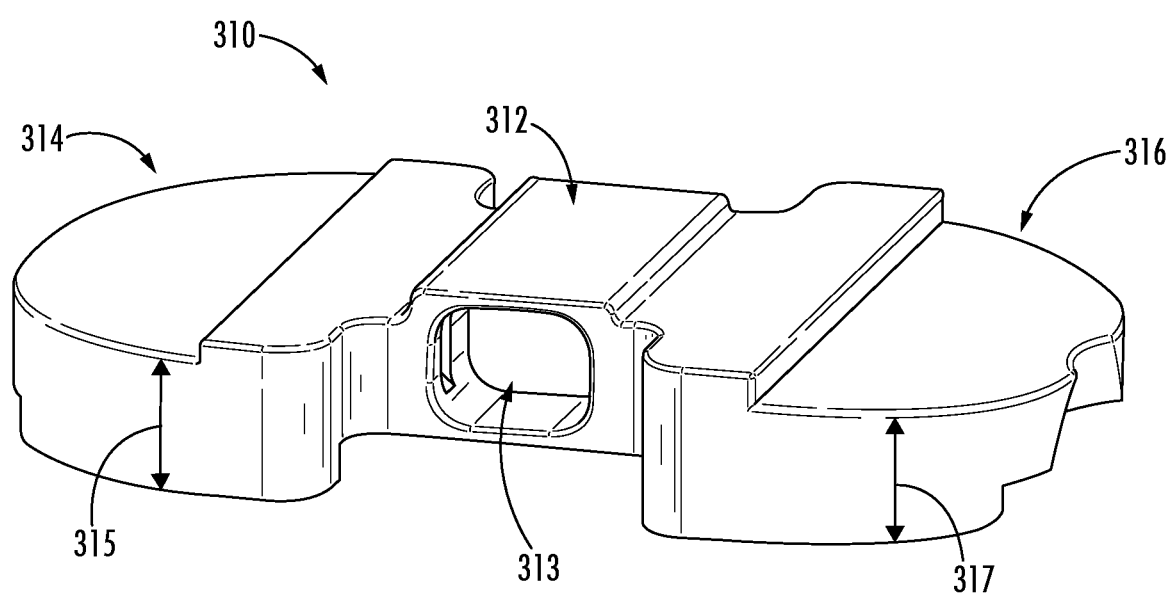
FIGS. 8 and 9 illustrate various perspective views of an example of an embodiment of flexion spacer blocks in accordance with certain principles of the present disclosure.

With additional reference to FIG. 8, operation 130 (FIG. 4) may begin with selecting the flexion spacer block 234. The spacer block may be any spacer block now known or hereafter developed. As illustrated, in one example of an embodiment, the flexion spacer block 234 may be in the form of a first spacer block 310. The spacer block 310 includes a body portion 312, a medial platform 314 positioned on a medial side of the body portion 312, and a lateral platform 316 positioned on an opposite lateral side of the body portion 312. The body portion 312 may include a cavity 313 configured to matingly engage with the handle 232 of the flexion gap assessment instrument 230 such that the spacer block 310 can be releasably coupled to the handle 232. The medial platform 314 has a first medial platform thickness 315, and the lateral platform 316 has a first lateral platform thickness 317. The first medial platform thickness 314 may correspond to the combined thickness of the baseplate of the tibial tray component 65 and the thinnest species of the insert 66. In certain forms, the first lateral platform thickness 317 may be the same as the first medial platform thickness 315. In the illustrated embodiment, however, the first lateral platform thickness 317 may be slightly greater than the first medial platform thickness 315. As a result, when the posterior medial condyle is in contact with the medial platform 314 and the posterior lateral condyle is in contact with the lateral platform 316 in the manner described herein, the femur 52 will be slightly rotated, for example by about one degree (1°), although other dimensions and configurations are envisioned.

Operation 130 may also involve placing the spacer block 310 in the flexion space 203 as previously described and placing the paddles 248 on the medial and lateral platforms 314, 316, respectively, such that the posterior femoral condyles rest on the paddles 248. If both the medial cruciate ligament (MCL) $58_M$ and the lateral cruciate ligament (LCL) $58_L$ are loose, a shim 236 may be coupled, attached, or the like, to the underside of the spacer block 310. This step may be repeated with shims 236 of increasing thickness until a desired tension is obtained in the MCL $58_M$. Each shim 236 corresponds to a respective species of the insert 66. Once appropriate tension has been achieved in the MCL $58_M$, the species of insert 66 corresponding to the appropriate shim 236 is noted. Further details regarding the shims 236 are provided below with reference to FIGS. 16, and 17-17B.

Figure 9:
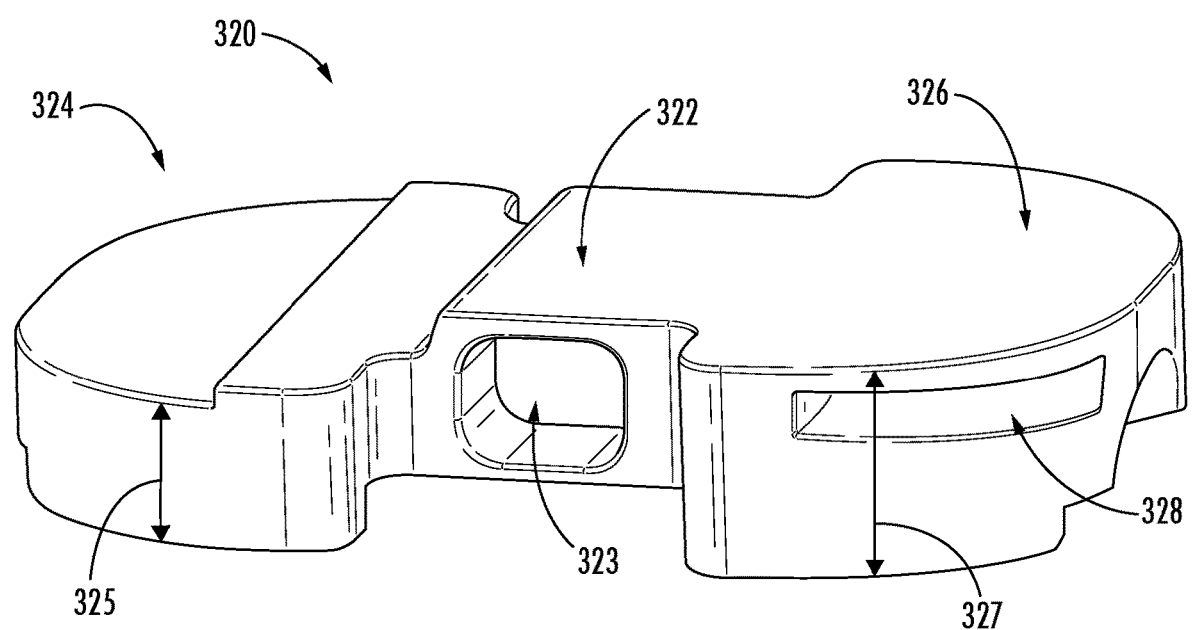

With additional reference to FIGS. 9-11, the process 100 (FIG. 4) may also include operation 140, which generally involves balancing the tension in the ligaments 58. In certain embodiments, operation 140 may be considered to be included in operation 130 that involves assessing the flexion space 203. In TKR procedures, it is often the case that the MCL $58_M$ is tighter than the LCL $58_L$. In order to take up this slack in the LCL $58_L$, operation 140 may involve the use of one or more stepped flexion spacer blocks. An example of an embodiment of a stepped flexion spacer block 320 is illustrated in FIG. 9. Similar to the first flexion spacer block 310, the stepped flexion spacer block 320 may include a body portion 322, a medial platform 324, and a lateral platform 326. The body portion 322 may also include a cavity 323. As illustrated, in use, the medial platform 324 includes a second medial platform thickness 325 and the lateral platform 326 includes a second lateral platform thickness 327. The second medial platform thickness 325 may be the same as the first medial platform thickness 315 such that the tension in the MCL $58_M$ remains substantially constant when using the different spacer blocks 310, 320. However, the second lateral platform thickness 327 may be greater than the first lateral platform thickness 317, which removes at least some of the slack from the LCL $58_L$.

Figure 20:
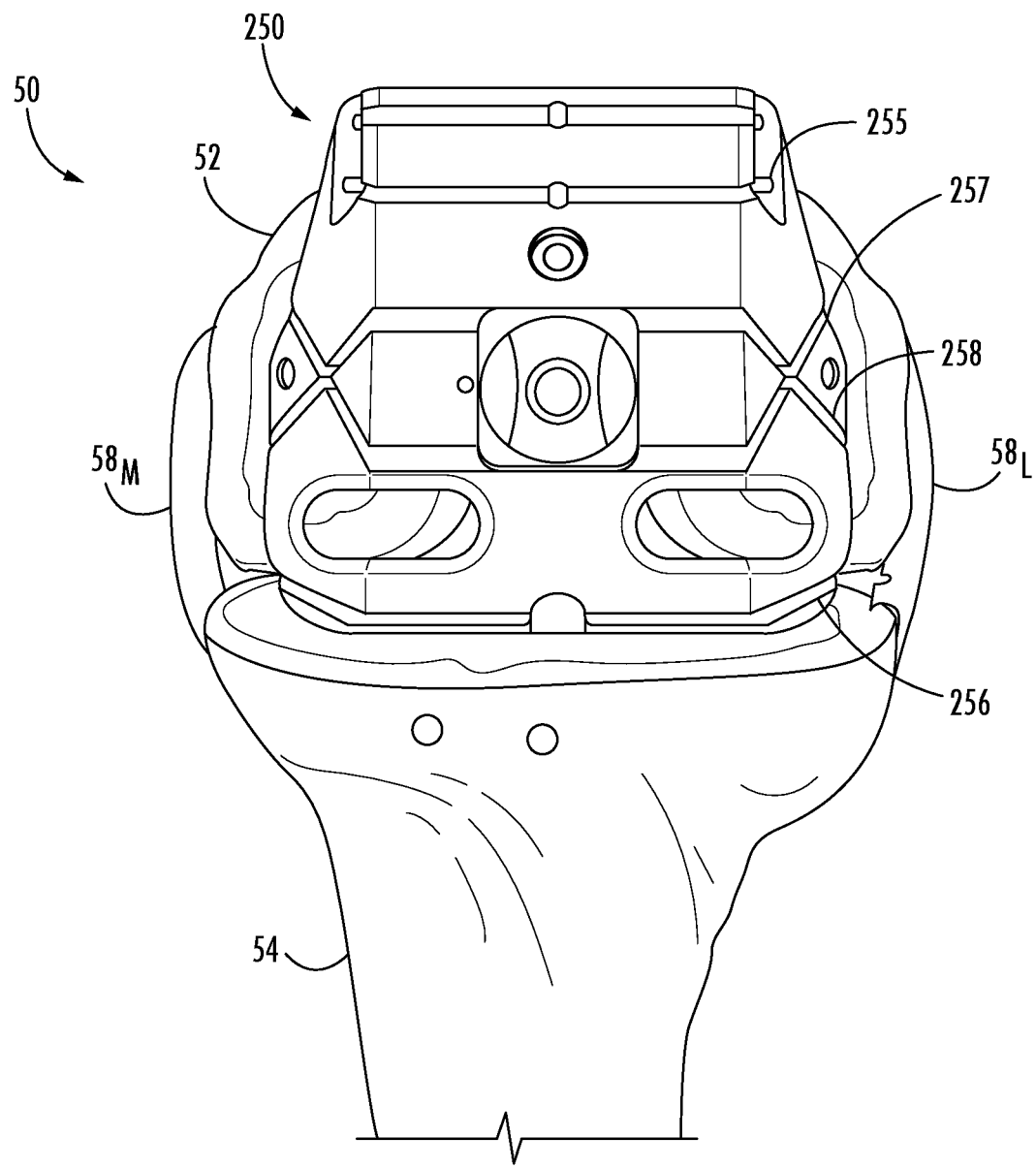
FIG. 20 illustrates the partially-resected knee with the cutting block mounted to the femur thereof.

The lateral platform 326 may also include a slot 328 that is sized and shaped to receive the paddle 248 (e.g., the lateral paddle 248) of the femoral sizing instrument 240. In one embodiment, the lower surface of the slot 328 may be substantially coplanar with the upper surface of the medial platform 324 such that when the paddles 248 are rested on these surfaces, the paddles 248 remain generally parallel to the proximal tibial resection surface 74 of the tibia 54. Due to the fact that the second lateral platform thickness 327 is greater than the first lateral platform thickness 317, the lateral posterior condyle is further removed from the resected tibial surface 74. This has the effects of increasing the tension in the LCL $58_L$, and of causing the femur 52 to be slightly rotated about the medial posterior condyle. As a result of the latter, the guide holes 243 may be positioned in a slightly different location as compared to the position of the guide holes 243 when the first spacer block 310 is used. As described herein, this altering of a position of the guide holes 243 leads to a different position and orientation for the anterior-posterior cutting block 250 (FIGS. 18-20).

With additional reference to FIG. 12, operation 140 (FIG. 4) may further involve utilizing at least one additional spacer block selected from a spacer block family 300. As generally illustrated, the spacer block family 300 includes a plurality of spacer blocks 302, including the first flexion spacer block 310 and one or more stepped flexion spacer blocks 304. In the illustrated form, the stepped flexion spacer blocks 304 include the second flexion spacer block 320, a third flexion spacer block 330, a fourth flexion spacer block 340, and a fifth flexion spacer block 350. As will be appreciated, it is also contemplated that the spacer block family 300 may include more or fewer species of the stepped flexion spacer blocks 304. Each of the stepped flexion spacer blocks 304 is substantially similar to the second flexion spacer block 320, and has a medial platform and a lateral platform. Each of the medial platforms may include the first medial platform thickness 315, and the lateral platforms may be of varying thickness from one spacer block to the next. Thus, the stepped spacer blocks 304 are configured to provide the femur 52 with varying rotational angles and to provide the LCL $58_L$ with varying degrees of tension.

Figure 13:
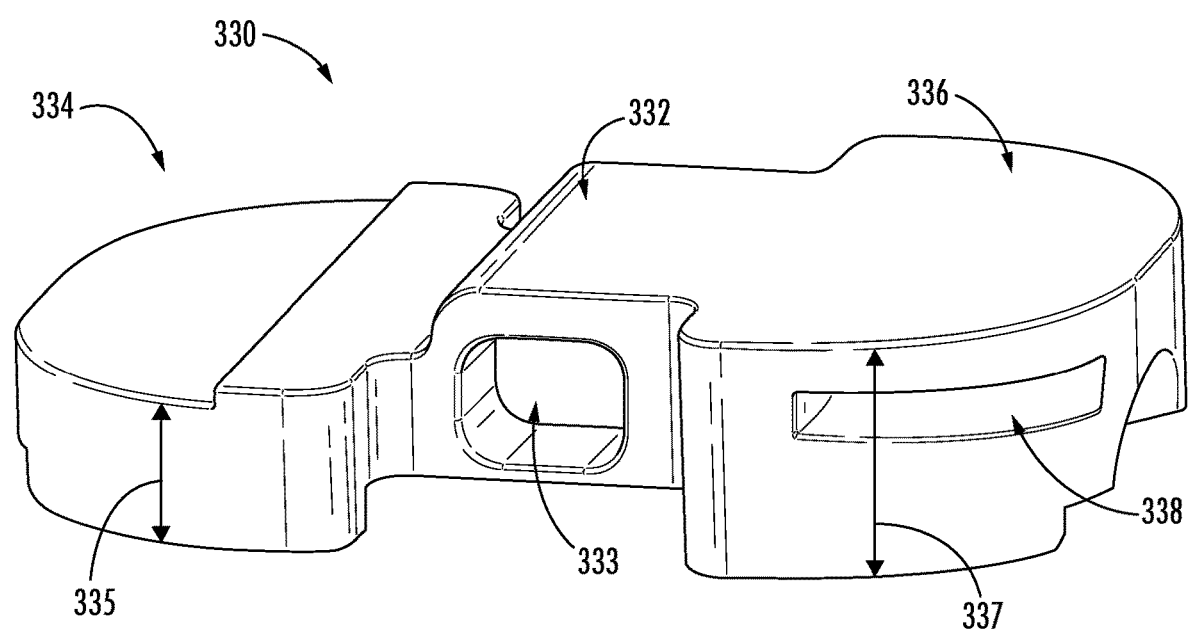
FIGS. 13-15 illustrate various perspective views of examples of embodiments of flexion spacer blocks in accordance with certain principles of the present disclosure.
Figure 14:
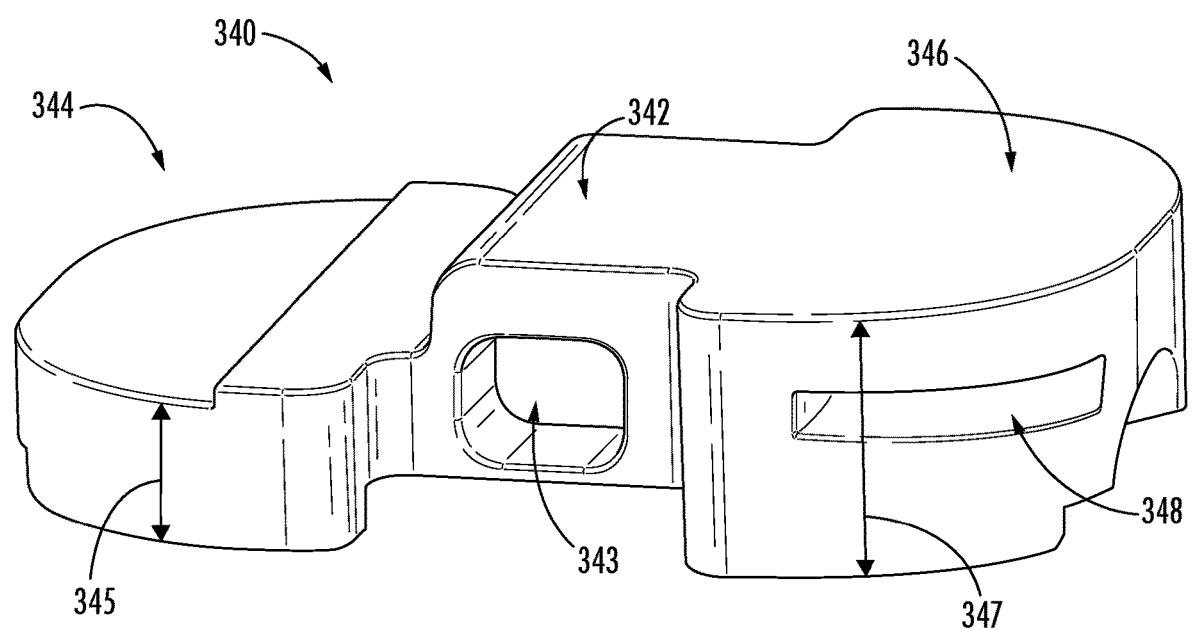
Figure 15:
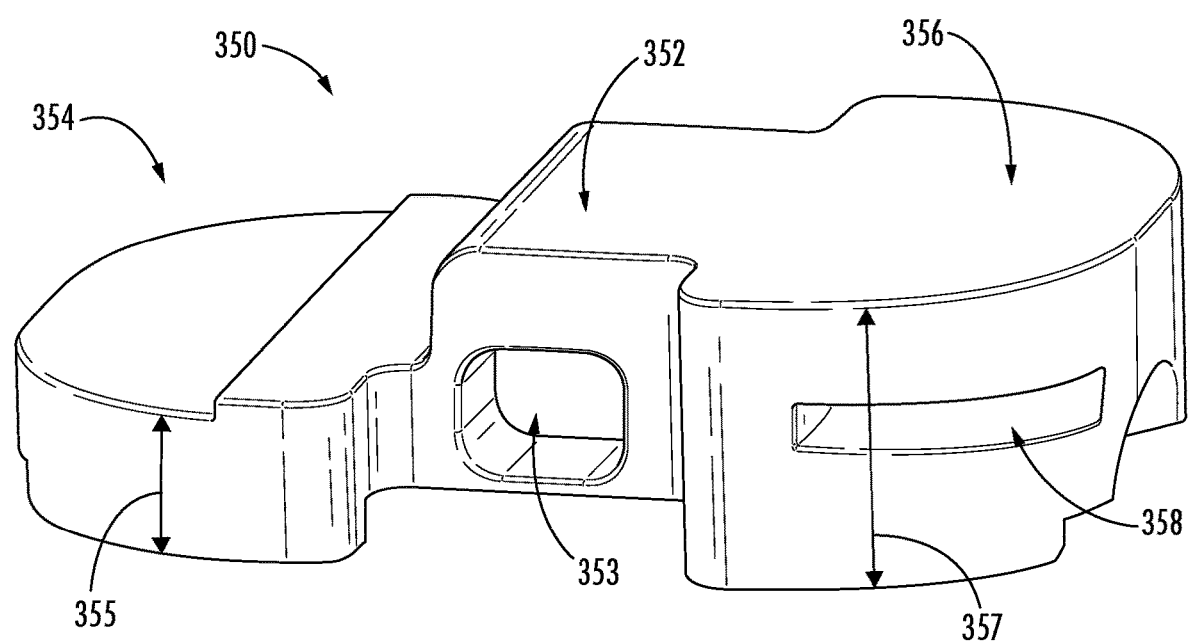

In the illustrated form, the first spacer block 310 may be configured to provide, for example, the femur 52 with a rotation angle of about one degree (1°), the second spacer block 320 may be configured to provide, for example, the femur 52 with a rotation angle of about three degrees (3°), and each of the additional spacer blocks may be configured to provide, for example, the femur 52 with a different rotation angle, although these are merely examples and other dimensions and configurations are envisioned. Exemplary forms of the additional spacer blocks 330, 340, 350 are illustrated in FIGS. 13-15. Each of the spacer blocks 330, 340, 350 is substantially similar to the second spacer block 320, and similar reference characters are used to indicate similar elements and features.

With additional reference to FIG. 13, the third flexion spacer block 330 may include a body portion 332 including a cavity 333, a medial platform 334 having a third medial platform thickness 335, and a lateral platform 336 having a third lateral platform thickness 337. The lateral platform 336 may include a receiving slot 338, the bottom surface of which may be substantially coplanar with the upper surface of the medial platform 334. The third medial platform thickness 335 may be substantially the same as the first medial platform thickness 315, and the third lateral platform thickness 337 may be greater than the second lateral platform thickness 327. Thus, the third flexion spacer block 330 is configured to provide the femur 52 with a greater rotation angle than the second flexion spacer block 320. By way of example, the third flexion spacer block 330 may be configured to provide the femur 52 with a rotation angle of about five degrees (5°).

With additional reference to FIG. 14, the fourth flexion spacer block 340 may include a body portion 342 including a cavity 343, a medial platform 344 having a fourth medial platform thickness 345, and a lateral platform 346 having a fourth lateral platform thickness 347. The lateral platform 346 may include a receiving slot 348, the bottom surface of which may be substantially coplanar with the upper surface of the medial platform 344. The fourth medial platform thickness 345 may be the same as the first medial platform thickness 315, and the fourth lateral platform thickness 347 may be greater than the third lateral platform thickness 337. Thus, the fourth flexion spacer block 340 is configured to provide the femur 52 with a greater rotation angle than is the third flexion spacer block 330. By way of example, the fourth flexion spacer block 340 may be configured to provide the femur 52 with a rotation angle of about seven degrees (7°).

With additional reference to FIG. 15, the fifth flexion spacer block 350 may include a body portion 352 including a cavity 353, a medial platform 354 having a fifth medial platform thickness 355, and a lateral platform 356 having a fifth lateral platform thickness 357. The lateral platform 356 may include a receiving slot 358, the bottom surface of which may be substantially coplanar with the upper surface of the medial platform 354. The fifth medial platform thickness 355 may be the same as the first medial platform thickness 315, and the fifth lateral platform thickness 357 may be greater than the fourth lateral platform thickness 347. Thus, the fifth flexion spacer block 350 is configured to provide the femur 52 with a greater rotation angle than is the fourth flexion spacer block 340. By way of example, the fifth flexion spacer block 350 may be configured to provide the femur 52 with a rotation angle of about nine degrees (9°).

In the illustrated embodiments, the spacer block family 300 includes five spacer blocks 302, which are configured to provide the femur 52 with varying degrees of rotation, although the spacer block family 300 may include more or fewer numbers of spacer blocks 302. More particularly, the five spacer blocks 310, 320, 330, 340, 350 are configured to provide the femur 52 with rotational angles ranging from one degree (1°) to nine degrees (9°) with a step or delta of two degrees (2°). It is also contemplated that greater or lesser rotational ranges may be provided. In certain forms, greater or lesser rotational ranges may be provided by including more or fewer spacer blocks. In certain forms, greater or lesser rotational ranges may be provided by altering the delta between spacer blocks, for example to one degree (1°) or three degrees (3°). In certain forms, a spacer block family 300 may include both a different number of spacer blocks than five and a different delta than two degrees (2°). Additionally, while the delta remains at a constant two degrees (2°) in the illustrated embodiment, it is also contemplated that the delta may vary within a spacer block family.

The spacer blocks 302 may include indicia that aid in performing the operation 140. For example, the spacer blocks 302 may include written indicia indicating which platform is to be engaged with the medial posterior condyle and/or which platform is to be engaged with the lateral posterior condyle. The spacer blocks 302 may additionally or alternatively include indicia that aid in differentiating the spacer blocks from one another. For example, the spacer blocks 302 may include written indicia identifying the degree of rotation the spacer block 302 is configured to impart to the femur 52. Additionally, or in the alternative, the spacer blocks 302 may be color coded to aid in distinguishing the spacer blocks 302 from one another. In the form illustrated in FIG. 12, the spacer blocks 302 include both written indicia and color-based indicia, although other forms of indicia are envisioned.

With additional reference to FIG. 16, illustrated therein is an example of an embodiment of a shim family 400 according to certain embodiments. As illustrated, the shim family 400 includes a plurality of shims 402, and in the illustrated form, may include first through eighth shims 410-480. Each of the shims 402 may be configured to include a different thickness, corresponding to a respective species of the insert 66, and may include indicia related to the corresponding species of insert 66.

Figure 17:
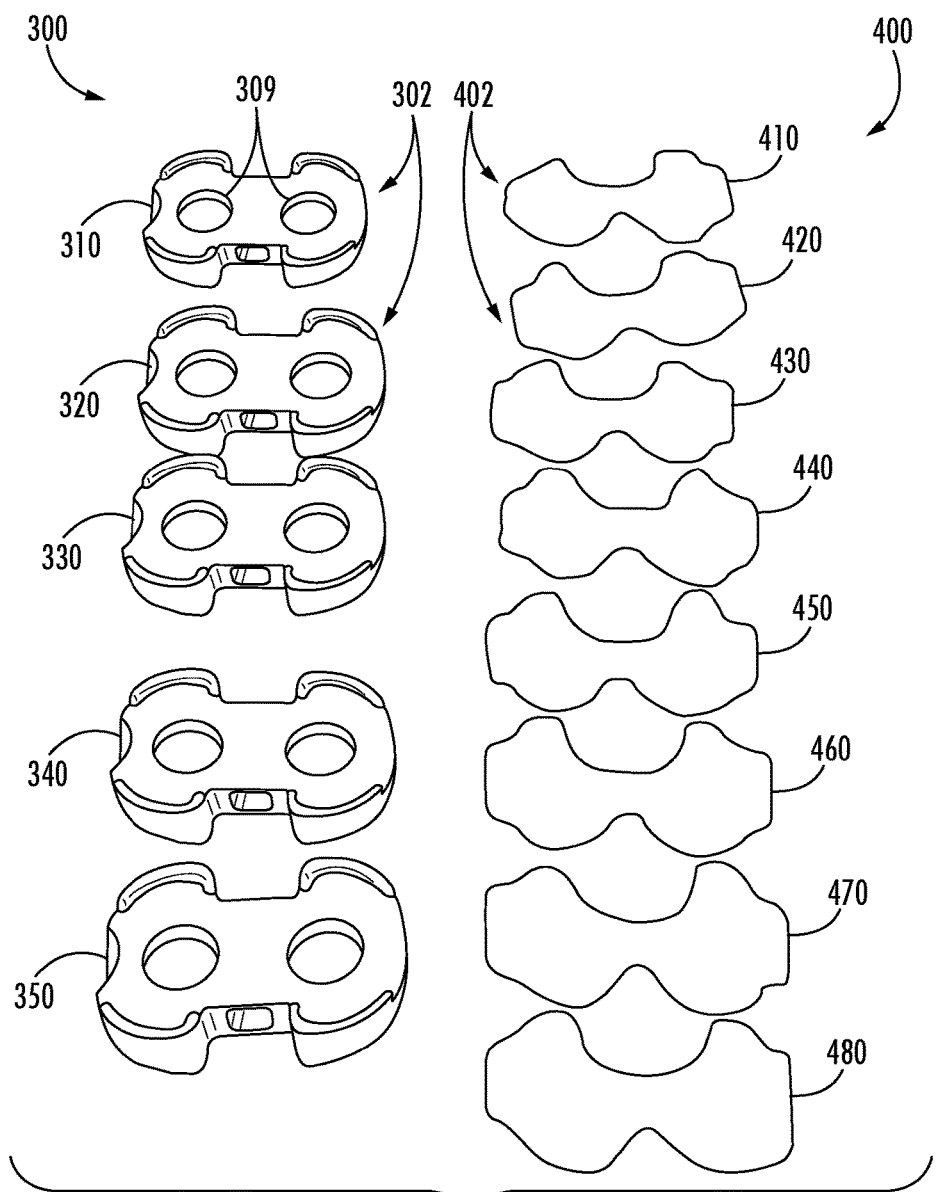
FIG. 17 illustrate perspective views of the flexion spacer block family and the shim family.
Figure 17A:
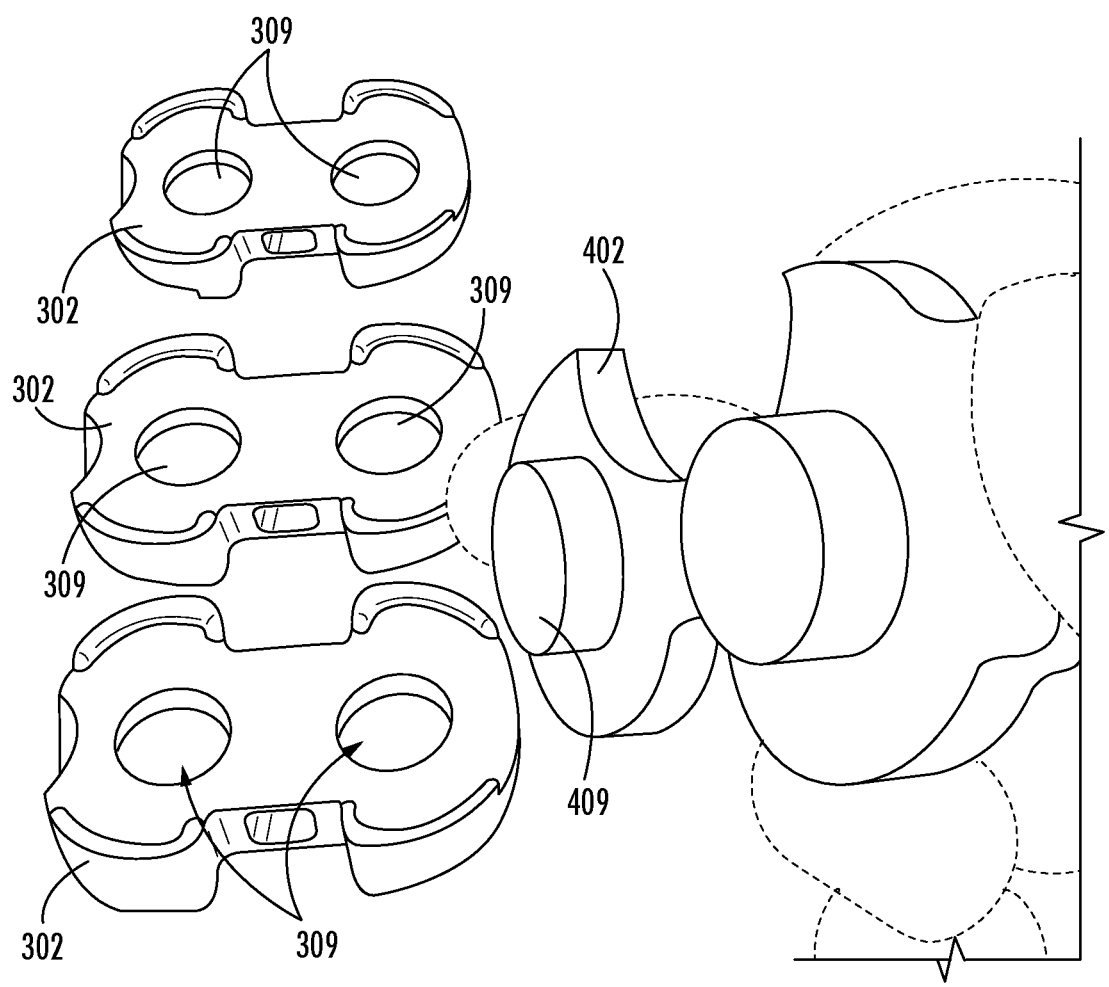
FIG. 17A illustrates a perspective, exploded view of a top surface of a shim arranged and configured to mate with a spacer block.
Figure 17B:
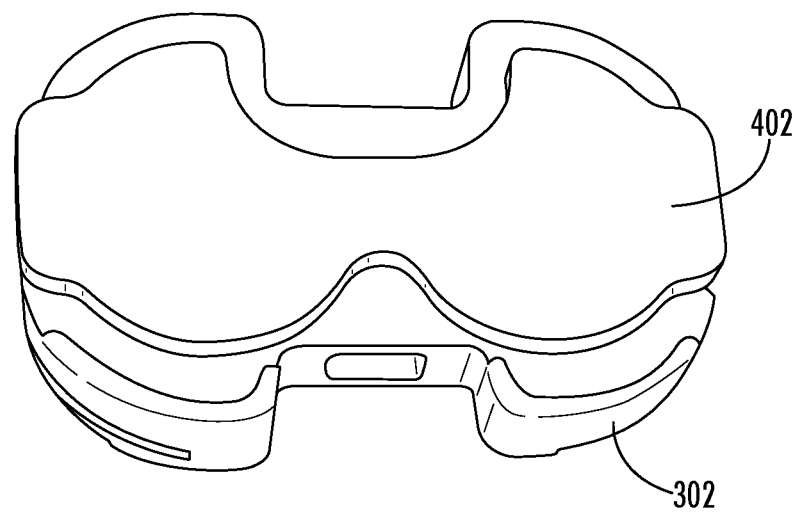
FIG. 17B illustrate a perspective view of the shim coupled to the spacer block.

With additional reference to FIG. 17, illustrated therein is an example of an embodiment of the spacer block family 300 along with an example of an embodiment of the shim family 400. As illustrated in FIGS. 17-17B, in one embodiment, an underside of each spacer block 302 may include a pair of cavities, recesses, or the like 309. Correspondingly, each shim 402 includes one surface (e.g., bottom surface) configured to mate, couple, engage, or the like the proximal tibial resection surface 74 of the tibia 54. In one embodiment, the surface (e.g., bottom surface) may be substantially flat for contacting with the proximal tibial resection surface 74 of the tibia 54. The opposite side (e.g., the top surface of the shims) is arranged and configured to mate with the underside of the spacer block 302. For example, in one embodiment, the opposite side (e.g., the top surface of the shims) may include a pair of posts, pegs, projections, or the like 409 configured to mate, couple, engage, or the like the cavities 309 formed in the spacer blocks 302. Thus arranged, each spacer block 302 in the spacer block family 300 may be configured to be used with each shim 402 in the shim family 400. In other words, the flexion spacer 238 can include any of the spacer blocks 302 as the spacer block 234 and any of the shims 402 as the shim 236.

As noted above, the flexion spacer blocks 302 may be configured to provide the femur 52 with various angles of rotation about the medial posterior condyle. As will be appreciated, greater degrees of rotation about the medial posterior condyle will result in increased tension for the LCL $58_L$, and may result in reduced tension for the MCL $58_M$. In the event that the tension in the MCL $58_M$ is reduced to a greater degree than is desired, a thicker shim 402 may be used to increase the tension in the MCL $58_M$. Thus, by selecting the appropriate combination of flexion spacer block 234 and shim 236, the ligaments 58 can be balanced.

Once the appropriate combination of a flexion spacer block 234 and shim 236 has been selected, the species of insert 66 selected based upon the extension balancing operation 120 is compared to the species of insert 66 selected based upon the flexion balancing operation 140. If the extension shim and the flexion shim correspond to the same species of insert 66, then the surgeon proceeds to operation 150 (FIG. 4). If the extension and flexion shims correspond to different species of the insert 66, the thicker insert may be selected, and adjustments may be made to the cuts or the femoral component sizes to ensure compatibility. Alternatively, a spacer, wedge, or shim could be added to the knee implant as is well known to those of ordinary skill in the art.

If the extension space 202 is tighter than the flexion space 203, the insert species selected based on the extension space 202 will be thinner than the insert species selected based on the flexion space 203. In such an event, the insert species selected based on the flexion space 203 (i.e., the thicker insert species) is selected for the insert 66. In order to balance the extension space 202 to the flexion space 203, additional bone can be removed from the distal femur 52 until the extension space 202 is of a size appropriate for the insert 66 (e.g., the insert species selected based on the flexion space 203).

Alternatively, if the flexion space 203 is tighter than the extension space 202, the insert species selected based on the extension space 202 will be thicker than the insert species selected based on the flexion space 203. In such an event, the insert species selected based on the extension space 202 (i.e., the thicker insert species) is selected for the insert 66. In order to balance the flexion space 203 to the extension space 202, a smaller size femoral component can be selected, and the AP cuts 75-78 (e.g., the anterior femur cut 75, the posterior femur cut 76, and anterior and posterior chamfer cuts 77, 78) can be shifted anteriorly to cut more bone off the posterior femur to ensure that the flexion space 203 is of the size appropriate for the insert 66. Such shifting may, for example, be accomplished by moving the first body portion 242 relative to the second body portion 244 before proceeding to operation 150.

Operation 150 generally involves setting the rotational alignment of the AP cutting block 250 using the femoral sizing instrument 240. Once the appropriate combination of a flexion spacer block 234 and shim 236 has been selected for the flexion spacer 238, the flexion spacer 238 is inserted into the flexion space 203, and the femoral sizing instrument 240 is placed in engagement with the flexion spacer 238. When the selected flexion spacer block 234 is the first spacer block 310, operation 150 may involve placing the paddles 248 on the upper surfaces of the platforms 314, 316 such that the paddles 248 are sandwiched between the platforms 314, 316 and the posterior condyles. When the selected flexion spacer block 234 is the second spacer block 304 or one of the other stepped spacer blocks 304, operation 150 may involve engaging the medial paddle 248 with the upper surface of the medial platform 324 and inserting the lateral paddle 248 into the receiving slot 328 in the lateral platform 326. In either event, the paddles 248 remain substantially parallel to the proximal tibial resection surface 74.

Once the femoral sizing instrument 240 is in position, the guide holes 243 are used to form pin holes 205 (FIG. 18) in the femur 52. This portion of operation 150 may, for example, involve inserting a drill bit of a drilling instrument through the guide holes 243 such that the drill bit engages the femoral resection surface 72 and forms the pin holes 205 therein.

With additional reference to FIGS. 18 and 19, the cutting block 250 may now be secured to the femur 52 using the pin holes 205. For example, as illustrated, the cutting block 250 may include a pair of posts or pins 251 that extend from the back side thereof, and which are sized and shaped to closely engage the pin holes 205. Operation 150 involves inserting these pins 251 into the pin holes 205 to couple the cutting block 250 to the femur 52.

With additional reference to FIG. 20, after mounting the cutting block 250 to the femur 52, the process 100 (FIG. 4) continues to operation 160, which generally involves forming the anterior-posterior resection cuts. As illustrated, the cutting block 250 includes a plurality of guide slots or cutting guides 255-258, each of which corresponds to a respective one of the resection cuts 75-78. More specifically, the cutting block 250 includes an anterior cutting guide 255 corresponding to the anterior resection cut 75, a posterior cutting guide 256 corresponding to the posterior resection cut 76, an anterior chamfer cutting guide 257 corresponding to the anterior chamfer cut 77, and a posterior chamfer guide 258 corresponding to the posterior chamfer cut 78. Operation 160 may include forming each of the cuts 75-78 using the corresponding cutting guide 275-278. For example, operation 160 may involve sequentially inserting a cutting instrument into each of the cutting guides 275-278 and operating the cutting instrument to form the resection cuts 75-78. The cutting block 250 is then removed from the resected femur 52.

With the resection cuts formed and the cutting block 250 removed from the femur 52, process 100 may continue to operation 170, which generally involves implanting the trial implant assembly 60 to the knee joint 50. More particularly, operation 170 involves implanting the femoral component 62 to the resected femur 52 and implanting the tibial component 64 to the resected tibia 54. Operation 170 may also include mounting the selected insert 66 to the tibial tray component 65 to form the tibial component 64.

In accordance with some of the principles of the present disclosure, the position and orientation of the implanted femoral component 62 relative to the femur 52 is directly related to the position and orientation of the cutting block 250, which in turn depends upon the position and orientation of the pin holes 205. Thus, by placing the pin holes 205 at the locations corresponding to balanced tension in the ligaments 58, the surgeon can implant the femoral component 62 at a location that will provide for better balance of the ligaments 58 both during extension and flexion. This represents an improvement over certain conventional techniques. This may enable the surgeon to perform the TKR procedure with less release of ligaments, and in some circumstances may wholly obviate the need for balancing by release.

As should be appreciated, the embodiments disclosed herein may provide for certain advantages over conventional approaches. Currently, surgeons use a rectangular spacer block to measure both the extension space and the flexion space, or may use a mechanical tensioner. These spacer blocks may be used after all the resection cuts have been made. Surgeons size the femur and set the rotation of the femoral implant off a femoral alignment sizing instrument. Tensioners may then be used. However, one problem with using conventional tensioners is that they pivot about the center point as opposed to maintaining the height of the medial portion. In such approaches, should the extension and flexion spaces be non-rectangular, the surgeon typically performs soft tissue releases to balance the knee. In the embodiments disclosed herein, however, the surgeon is able to balance the flexion space and set rotation and placement of the AP cutting block 250 prior to making any rotational femoral cuts. This may reduce or eliminate the need to perform soft tissue adjustments for balancing.

In the illustrated form, the rotational positioning of the femur 52 is performed using the flexion spacer 238, which includes the flexion spacer block 234 and which may further include the shim 236. In other embodiments, the rotational positioning of the femur may be accomplished in another manner. For example, the spacer 238 could be replaced by the femoral sizing instrument 240 if the instrument 240 were adapted to pivot about the medial paddle 248 and was provided with sufficient adjustability. In certain embodiments, the femoral rotation can be set off a femoral sizing guide that is set at zero degrees and placed into the flexion spacer 238 where the paddles 248 of the femoral sizing instrument 240 are parallel to the tibial resection surface 74 and the posterior femoral condyles are against the angled flexion spacer block 234. In other embodiments, the discrete spacer blocks 234 may be replaced by a single adjustable spacer block including a mechanical adjustment mechanism.

In certain embodiments, the femoral rotation can be set based upon the flexion spacer 238 with a separate femoral sizing drill guide that is operable to rotate throughout a predetermined angular span, such as a span of fifteen degrees (15°). The femoral rotation can also be set with an angled flexion spacer that is stepped and that takes into consideration the posterior condyle thickness. The stepped part of the spacer 238 is parallel to the tibial resection surface 74, and the AP cutting block 250 is placed on the stepped surface while the angled surface is in contact with the posterior condyles and the AP cutting block 250 is fixed onto the distal femur. Alternatively, femoral rotation can also be accomplished with an anterior femoral cutting block that makes a parallel anterior cut to the flexion spacer block surface of the tibia.

While the invention has been illustrated and described in detail in the drawings and foregoing description, the same is to be considered as illustrative and not restrictive in character, it being understood that only the preferred embodiments have been shown and described and that all changes and modifications that come within the spirit of the inventions are desired to be protected. For example, in the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures unless indicated to the contrary. Additionally, the inclusion of a structural or method feature in a particular figure is not meant to imply that such feature is required in all embodiments and, in some embodiments, may not be included or may be combined with other features.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. It should further be appreciated that although reference to a "preferred" component or feature may indicate the desirability of a particular component or feature with respect to an embodiment, the disclosure is not so limiting with respect to other embodiments, which may omit such a component or feature. Further, when a particular feature, structure, or characteristic is described in connection with an embodiment, it is submitted that it is within the knowledge of one skilled in the art to implement such feature, structure, or characteristic in connection with other embodiments whether or not explicitly described. Additionally, it should be understood that while the use of words such as preferable, preferably, preferred or more preferred utilized in the description above indicate that the feature so described may be more desirable, it nonetheless may not be necessary and embodiments lacking the same may be contemplated as within the scope of the invention, the scope being defined by the claims that follow.

While the present disclosure refers to certain embodiments, numerous modifications, alterations, and changes to the described embodiments are possible without departing from the sphere and scope of the present disclosure, as defined in the appended claim(s). Accordingly, it is intended that the present disclosure not be limited to the described embodiments, but that it has the full scope defined by the language of the following claims, and equivalents thereof. The discussion of any embodiment is meant only to be explanatory and is not intended to suggest that the scope of the disclosure, including the claims, is limited to these embodiments. In other words, while illustrative embodiments of the disclosure have been described in detail herein, it is to be understood that the inventive concepts may be otherwise variously embodied and employed, and that the appended claims are intended to be construed to include such variations, except as limited by the prior art.

The foregoing discussion has been presented for purposes of illustration and description and is not intended to limit the disclosure to the form or forms disclosed herein. For example, various features of the disclosure are grouped together in one or more embodiments or configurations for the purpose of streamlining the disclosure. However, it should be understood that various features of the certain embodiments or configurations of the disclosure may be combined in alternate embodiments, or configurations. Moreover, the following claims are hereby incorporated into this Detailed Description by this reference, with each claim standing on its own as a separate embodiment of the present disclosure.

The device and associated methods in accordance with the present disclosure have been described with reference to particular embodiments thereof. Therefore, the above description is by way of illustration and not by way of limitation. Accordingly, it is intended that all such alterations and variations and modifications of the embodiments are within the scope of the present invention as defined by the appended claims.

While the methods disclosed herein have been described and shown with reference to particular steps performed in a particular order, it will be understood that these steps may be combined, subdivided, or re-ordered to form an equivalent method without departing from the teachings of the present disclosure. Accordingly, unless specifically indicated herein, the order and grouping of the steps are not generally intended to be a limitation of the present disclosure.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The phrases "at least one", "one or more", and "and/or", as used herein, are open-ended expressions that are both conjunctive and disjunctive in operation. The terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present disclosure, and do not create limitations, particularly as to the position, orientation, or use of this disclosure. Connection references (e.g., engaged, attached, coupled, connected, and joined) are to be construed broadly and may include intermediate members between a collection of elements and relative to movement between elements unless otherwise indicated. As such, connection references do not necessarily infer that two elements are directly connected and in fixed relation to each other. All rotational references describe relative movement between the various elements. Identification references (e.g., primary, secondary, first, second, third, fourth, etc.) are not intended to connote importance or priority but are used to distinguish one feature from another. The drawings are for purposes of illustration only and the dimensions, positions, order and relative to sizes reflected in the drawings attached hereto may vary.

What is claimed is:

1. A method for balancing a patient's medial cruciate ligament (MCL) and lateral cruciate ligament (LCL) in a knee including a femur and a tibia; the method comprising:
   forming a first resection cut in the femur to form a femoral resected surface;
   forming a second resection cut in the tibia to form a tibia resected surface;
   placing the knee in flexion to define a flexion space, the flexion space being defined by the femoral and tibia resected surfaces;
   inserting a first flexion spacer block into the flexion space;
   removing the first flexion spacer block;
   sequentially inserting one or more additional flexion spacer blocks including at least a second flexion spacer block into the flexion spacer to select a flexion spacer block that balances the MCL and LCL with equal tension; wherein each of the flexion spacer blocks includes a central body portion, a medial platform, and a lateral platform, the medial platform having a medial platform thickness, the lateral platform having a lateral platform thickness, the lateral platform thickness of the second flexion spacer block being greater than the lateral platform thickness of the first flexion spacer block, the medial platform thickness of the second flexion spacer block being equal to the medial platform thickness of the first flexion spacer block;
   placing the knee in extension and, with the knee in extension, assessing an extension space formed between the femoral resection surface and the tibial resection surface, wherein assessing the extension space includes inserting extension spacers of different sizes into the extension space until the MCL and LCL have equal tension; and
   selecting an insert of a tibial component from a plurality of available inserts having varying thicknesses, wherein selecting the insert comprises:
      selecting a first insert species from a plurality of insert species based upon the selected flexion spacer block;
      selecting a second insert species from a plurality of insert species based upon the selected extension spacer;
   wherein:
      if the first insert species and the second insert species are one species, selecting the one species for the insert;
      if the first insert species has a larger thickness than the second insert species, selecting the first insert species for the insert; and
      if the first insert species has a smaller thickness than the second insert species, selecting the second insert species for the insert.

2. The method of claim 1, wherein sequentially inserting one or more additional flexion spacer blocks including at least a second flexion spacer block into the flexion spacer comprises:
   inserting the second flexion spacer block into the flexion spacer, and in response to the LCL having less tension than the MCL, removing the second flexion spacer block and inserting a third flexion spacer block;
   wherein the third flexion spacer block includes a central body portion, a medialplatform, and a lateral platform, the medial platform having a medial platform thickness, the lateral platform having a lateral platform thickness, the lateral platform thickness of the third flexion spacer block being greater than the lateral platform thickness of the first and second flexion spacer block, the medial platform thickness of the third flexion spacer block being equal to the medial platform thickness of the first and second flexion spacer blocks.

3. The method of claim 1, wherein inserting a first flexion spacer block into the flexion space and sequentially inserting one or more additional flexion spacer blocks including at least a second flexion spacer block into the flexion spacer comprises:
   engaging a lower surface of each flexion spacer block with the tibial resection surface;
   engaging an upper surface of the medial platform with a posterior medial condyle of the femur; and
   engaging an upper surface of the lateral platform with a posterior lateral condyle of the femur.

4. The method of claim 1, further comprising:
   coupling an alignment sizing instrument to the selected flexion spacer block;

forming a pair of pin holes in the patient's femur using the alignment sizing instrument; and coupling a cutting block to the patient's femur using the formed pin holes.

5. The method of claim 4, wherein the alignment sizing instrument includes an anterior guide slot, a posterior guide slot, an anterior chamfer guide slot, and a posterior chamfer guide slot; the method further comprising:

forming an anterior cut using the anterior guide slot, forming a posterior cut using the posterior guide slot, forming an anterior chamfer cut using the anterior chamfer guide slot, and forming a posterior chamfer cut using the posterior chamfer guide slot.

6. A method for balancing a patient's medial cruciate ligament (MCL) and lateral cruciate ligament (LCL) in a knee including a femur and a tibia; the method comprising:

forming at least a first resection cut in the femur to form a femoral resected surface;

placing the knee in flexion to define a flexion space;

inserting a first flexion spacer block into the flexion space;

removing the first flexion spacer block; and sequentially inserting one or more additional flexion spacer blocks including at least a second flexion spacer block into the flexion spacer to select a flexion spacer block that balances the MCL and LCL with equal tension;

wherein, during use, the first flexion spacer block is arranged and configured to position the femur in a first position relative to the tibia; each additional flexion spacer block including at least the second flexion spacer block is arranged and configured to position the femur in a different position relative to the tibia, each of the different positions being rotationally offset from the first position; and wherein inserting each flexion spacer block into the flexion space comprises engaging a lower surface of each flexion spacer block with the tibial resection surface; engaging an upper surface of the medial platform with a posterior medial condyle of the femur; and engaging an upper surface of the lateral platform with a posterior lateral condyle of the femur.

7. The method of claim 6, wherein forming at least a first resection cut in the femur to form a femoral resected surface, further comprises forming a second resection cut in the tibia to form a tibia resected surface; the flexion space being defined by the femoral and tibia resected surfaces.

8. The method of claim 7, further comprising:

placing the knee in extension and, with the knee in extension, assessing an extension space formed between the femoral resection surface and the tibial resection surface, wherein assessing the extension space includes inserting extension spacers of different sizes into the extension space until the MCL and LCL have equal tension.

9. The method of claim 8, further comprising:

selecting an insert of a tibial component from a plurality of available inserts based at least in part upon the selected extension spacer, wherein the plurality of available inserts includes inserts having varying thicknesses.

10. The method of claim 9, wherein selecting an insert comprises:

selecting a first insert species from a plurality of insert species based upon the selected flexion spacer block;

selecting a second insert species from a plurality of insert species based upon the selected extension spacer;

wherein:

if the first insert species and the second insert species are one species, selecting the one species for the insert;

if the first insert species has a larger thickness than the second insert species, selecting the first insert species for the insert; and if the first insert species has a smaller thickness than the second insert species, selecting the second insert species for the insert.

11. The method of claim 6, further comprising:

selecting an insert of a tibial component from a plurality of available inserts based at least in part upon the selected flexion spacer block, wherein the plurality of available inserts includes inserts having varying thicknesses.

12. The method of claim 6, wherein sequentially inserting one or more additional flexion spacer blocks including at least a second flexion spacer block into the flexion spacer comprises:

inserting the second flexion spacer block into the flexion spacer, and in response to the LCL having less tension than the MCL, removing the second flexion spacer block and inserting a third flexion spacer block;

wherein the third flexion spacer block includes a central body portion, a medialplatform, and a lateral platform, the medial platform having a medial platform thickness, the lateral platform having a lateral platform thickness, the lateral platform thickness of the third flexion spacer block being greater than the lateral platform thickness of the first and second flexion spacer block, the medial platform thickness of the third flexion spacer block being equal to the medial platform thickness of the first and second flexion spacer blocks.

13. The method of claim 6, further comprising:

coupling an alignment sizing instrument to the selected flexion spacer block;

forming a pair of pin holes in the patient's femur using the alignment sizing instrument; and coupling a cutting block to the patient's femur using the formed pin holes.

14. The method of claim 13, wherein the alignment sizing instrument includes an anterior guide slot, a posterior guide slot, an anterior chamfer guide slot, and a posterior chamfer guide slot; the method further comprising:

forming an anterior cut using the anterior guide slot, forming a posterior cut using the posterior guide slot, forming an anterior chamfer cut using the anterior chamfer guide slot, and forming a posterior chamfer cut using the posterior chamfer guide slot.

15. A method for balancing a patient's medial cruciate ligament (MCL) and lateral cruciate ligament (LCL) in a knee including a femur and a tibia;

the method comprising:

forming at least a first resection cut in the femur to form a femoral resected surface;

placing the knee in flexion to define a flexion space;

inserting a first flexion spacer block into the flexion space;

removing the first flexion spacer block; and sequentially inserting one or more additional flexion spacer blocks including at least a second flexion spacer block into the flexion spacer to select a flexion spacer block that balances the MCL and LCL with equal tension;

coupling an alignment sizing instrument to the selected flexion spacer block that balances the MCL and LCL with equal tension;

forming a pair of pin holes in the patient's femur using the alignment sizing instrument; and coupling a cutting block to the patient's femur using the formed pin holes;

wherein each of the flexion spacer blocks includes a central body portion, a medialplatform, and a lateral platform, the medial platform having a medial platform thickness, the lateral platform having a lateral platform thickness, the lateral platform thickness of the second flexion spacer block being greater than the lateral platform thickness of the first flexion spacer block, the medial platform thickness of the second flexion spacer block being equal to the medial platform thickness of the first flexion spacer block.

16. The method of claim 15, wherein forming at least a first resection cut in the femur to form a femoral resected surface, further comprises forming a second resection cut in the tibia to form a tibia resected surface; the flexion space being defined by the femoral and tibia resected surfaces.

17. The method of claim 16, further comprising:
placing the knee in extension and, with the knee in extension, assessing an extension space formed between the femoral resection surface and the tibial resection surface, wherein assessing the extension space includes inserting extension spacers of different sizes into the extension space until the MCL and LCL have equal tension.

18. The method of claim 17, further comprising:
selecting an insert of a tibial component from a plurality of available inserts based at least in part upon the selected extension spacer, wherein the plurality of available inserts includes inserts having varying thicknesses.

19. The method of claim 18, wherein selecting an insert comprises:
selecting a first insert species from a plurality of insert species based upon the selected flexion spacer block;
selecting a second insert species from a plurality of insert species based upon the selected extension spacer;
wherein:
if the first insert species and the second insert species are one species, selecting the one species for the insert;
if the first insert species has a larger thickness than the second insert species, selecting the first insert species for the insert; and
if the first insert species has a smaller thickness than the second insert species, selecting the second insert species for the insert.

20. The method of claim 15, further comprising:
selecting an insert of a tibial component from a plurality of available inserts based at least in part upon the selected flexion spacer block, wherein the plurality of available inserts includes inserts having varying thicknesses.

21. The method of claim 15, wherein sequentially inserting one or more additional flexion spacer blocks including at least a second flexion spacer block into the flexion spacer comprises:
inserting the second flexion spacer block into the flexion spacer, and in response to the LCL having less tension than the MCL, removing the second flexion spacer block and inserting a third flexion spacer block;
wherein the third flexion spacer block includes a central body portion, a medialplatform, and a lateral platform, the medial platform having a medial platform thickness, the lateral platform having a lateral platform thickness, the lateral platform thickness of the third flexion spacer block being greater than the lateral platform thickness of the first and second flexion spacer block, the medial platform thickness of the third flexion spacer block being equal to the medial platform thickness of the first and second flexion spacer blocks.

22. The method of claim 15, wherein inserting a first flexion spacer block into the flexion space and sequentially inserting one or more additional flexion spacer blocks including at least a second flexion spacer block into the flexion spacer comprises:
engaging a lower surface of each flexion spacer block with the tibial resection surface;
engaging an upper surface of the medial platform with a posterior medial condyle of the femur; and
engaging an upper surface of the lateral platform with a posterior lateral condyle of the femur.

23. The method of claim 15, wherein the alignment sizing instrument includes an anterior guide slot, a posterior guide slot, an anterior chamfer guide slot, and a posterior chamfer guide slot; the method further comprising:
forming an anterior cut using the anterior guide slot, forming a posterior cut using the posterior guide slot, forming an anterior chamfer cut using the anterior chamfer guide slot, and forming a posterior chamfer cut using the posterior chamfer guide slot.

* * * * *